(12) United States Patent
Kumar

(10) Patent No.: US 9,068,004 B2
(45) Date of Patent: Jun. 30, 2015

(54) TWEAK/FN14 SYSTEM REGULATES SKELETAL MUSCLE ATROPHY AND REGENERATION

(75) Inventor: Ashok Kumar, Louisville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 0 days.

(21) Appl. No.: 13/576,838

(22) PCT Filed: Feb. 4, 2011

(86) PCT No.: PCT/US2011/023774
§ 371 (c)(1),
(2), (4) Date: Aug. 2, 2012

(87) PCT Pub. No.: WO2011/097500
PCT Pub. Date: Aug. 11, 2011

(65) Prior Publication Data
US 2013/0028912 A1    Jan. 31, 2013

Related U.S. Application Data

(60) Provisional application No. 61/301,454, filed on Feb. 4, 2010.

(51) Int. Cl.
*A61K 39/395* (2006.01)
*C07K 16/28* (2006.01)
*A61K 39/00* (2006.01)

(52) U.S. Cl.
CPC ....... *C07K 16/2875* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 6,727,225 B2 | 4/2004 | Wiley |
| 6,824,773 B2 | 11/2004 | Wiley |
| 7,169,387 B2 | 1/2007 | Rennert |
| 7,208,151 B2 | 4/2007 | Browning et al. |
| 7,579,001 B2 | 8/2009 | Rennert |
| 7,732,588 B2 | 6/2010 | Wiley |
| 8,506,958 B2 | 8/2013 | Burkly et al. |
| 2006/0003932 A1 | 1/2006 | Jakubowski et al. |
| 2006/0127397 A1 | 6/2006 | Strittmatter |
| 2006/0240004 A1 | 10/2006 | Burkly et al. |
| 2007/0110745 A1 | 5/2007 | Rennert |
| 2008/0187544 A1 | 8/2008 | Burkly et al. |
| 2008/0241163 A1 | 10/2008 | Burkly et al. |

(Continued)

FOREIGN PATENT DOCUMENTS

| | | |
|---|---|---|
| EP | 1566636 A1 | 8/2005 |
| WO | WO 03/086311 A2 | 10/2003 |

OTHER PUBLICATIONS

Bigard et al., "Muscle Unloading Induces Slow to Fast Transitions in Myofibrillar but not Mitochondrial Properties. Relevance to Skeletal Muscle Abnormalities in Heart Failure",*J. Mol. Cell Cardiol*, 30, 2391-2401 (1998).

(Continued)

*Primary Examiner* — Claire Kaufman
(74) *Attorney, Agent, or Firm* — Viksnins Harris & Padys PLLP

(57) ABSTRACT

The invention provides methods for preventing loss and augmenting regeneration of skeletal muscle by decreasing the activity of the TWEAK/Fn14 system.

17 Claims, 28 Drawing Sheets

(56) References Cited

U.S. PATENT DOCUMENTS

| | | | |
|---|---|---|---|
| 2008/0279853 | A1 | 11/2008 | Burkly et al. |
| 2009/0068102 | A1 | 3/2009 | Burkly et al. |
| 2009/0124993 | A1 | 5/2009 | Burkly et al. |
| 2009/0137036 | A1 | 5/2009 | Kim et al. |
| 2009/0311313 | A1 | 12/2009 | Burkly et al. |
| 2009/0324602 | A1 | 12/2009 | Garber et al. |
| 2010/0061985 | A1 | 3/2010 | Rennert |
| 2010/0255008 | A1 | 10/2010 | Baehner et al. |
| 2010/0272721 | A1 | 10/2010 | Burkly et al. |
| 2010/0284933 | A1 | 11/2010 | Burkly |

OTHER PUBLICATIONS

Bodine et al., "Identification of Ubiquitin Ligases Required for Skeletal Muscle Atrophy", *Science*, 294, 1704-1708 (2001).

Dogra et al., "TNF-related weak inducer of apoptosis (TWEAK) is a potent skeletal muscle-wasting cytokine", *The FASEB Journal*, vol. 21, 1857-1869 (2007).

Girgenrath et al., "TWEAK, via its receptor Fn14, is a novel regulator of mesenchymal progenitor cells and skeletal muscle regeneration", *The EMBO Journal*, 25, 5826-5839 (2006).

Glass, "Signalling pathways that mediate skeletal muscle hypertrophy and atrophy", *Nat. Cell Biol.*, vol. 5, 87-90 (2003).

Glass, "Skeletal muscle hypertrophy and atrophy signaling pathways", *Int. J. Biochem. Cell Biol.*, 37, 1974-1984 (2005).

Gomes et al., "Atrogin-1, a muscle-specific F-box protein highly expressed during muscle atrophy", *Proc. Natl. Acad. Sci.*, vol. 98 (25), 14440-14445 (2001).

Jackman et al., "The molecular basis of skeletal muscle atrophy", *Am J. Physiol Cell Physiol.*, 287, C834-C843 (2004).

Kumar et al., "The TWEAK-Fn 14 system is a critical regulator of denervation-induced skeletal muscle atrophy in mice", *J. Cell Biol.* vol. 188 (6), 833-849 (2010).

Macaluso et al., "Muscle strength, power and adaptations to resistance training in older people", *Eur J. Appl Physiol.*, 91, 450-472 (2004).

McKinnell et al., "Muscle Stem Cells and Regenerative Myogenesis", *Curr Top Dev Biol.*, 71, 113-130 (2005).

Mittal et al., "The TWEAK-Fn 14 system is a critical regulator of denervation-induced skeletal muscle atrophy in mice", *J. Cell Biol.*, vol. 188 (6), 833-849 (2010).

Patent Cooperation Treaty, International Searching Authority, Search Report and Written Opinion for PCT/US2011/023774, 13 pages, Oct. 18, 2011.

Sandri, "Signaling in Muscle Atrophy and Hypertrophy", *Physiology*, 23, 160-170 (2008).

Al-Sawaf et al., "Nrf2 protects against TWEAK-mediated skeletal muscle wasting", *Scientific Reports* 4, 3625, 7 pages (2014).

Bhatnagar et al., "TWEAK induces myotube atrophy through coordinated activation of ubiquitin-proteasome system, autophagy, and caspases", *Journal of Cellular Physiology*, 227 (3), 1042-1051 (2012).

Dogra et al., "Fibroblast Growth Factor Inducible 14 (Fn14) is Required for the Expression of Myogenic Regulatory Factors and Differentiation of Myoblasts into Myotubes", *Journal of Biological Chem.* 282 (20), 15000-15010 (2007).

Finlin et al., "DHA reduces the atrophy-associated Fn14 protein in differentiated myotubes during coculture with macrophages", *J Nutr Biochem* 23, 885-891 (2012).

Hindi et al., "Regulatory circuitry of Tweak-Fn14 system and PGC-1α in skeletal muscle atrophy program", *FASEB Journal*, 28, 1398-1411 (2014).

Merritt et al., "Increased expression of atrogenes and TWEAK family members after severe burn injury in nonburned human skeletal muscle", *J Burn Care Res* 34, e297-304 (2013).

Mittal et al., "Genetic Ablation of TWEAK Augments Regeneration and Post-Injury Growth of Skeletal Muscle in Mice", *American Journal of Pathology*, 177 (4), 1732-1742 (2010).

Morosetti et al., "TWEAK in inclusion-body myositis muscle: possible pathogenic role of a cytokine inhibiting myogenesis", *Am J Pathol* 180 (4), 1603-1613 (2012).

Ogura et al., "Proinflammatory cytokine tumor necrosis factor (TNF)-like weak inducer of apoptosis (TWEAK) suppresses satellite cell self-renewal through inversely modulating Notch and NF-κB signaling pathways", *Journal of Biological Chemistry*, 288 (49), 35159-35169 (2013).

Sato et al., "TWEAK/Fn14 signaling axis mediates skeletal muscle atrophy and metabolic dysfunction", *Frontiers in Immunology*, 5, 18 (1-10 pp) (2014).

Tajrishi et al., "The TWEAK-Fn14 dyad is involved in age-associated pathological changes in skeletal muscle", *Biochemical and Biophysical Research Communications*, 446, 1219-1224 (2014).

Tajrishi et al., "DNA methyltransferase 3a and mitogen-activated protein kinase signaling regulate the expression of fibroblast growth factor-inducible 14 (Fn14) during denervation-induced skeletal muscle atrophy", *Journal of Biological Chemistry*, 289 (29), 19985-19999 (2014).

Tajrishi et al., "The TWEAK/Fn14 pathway: A potent regulator of skeletal muscle biology in health and disease", *Cytokine & Growth Factor Review*, 25, 215-225 (2014).

Wu et al., "Identification of genes that elicit disuse muscle atrophy via the transcription factors p50 and Bcl-3", *PLoS One* 6(1), e16171, 9 pages (2011).

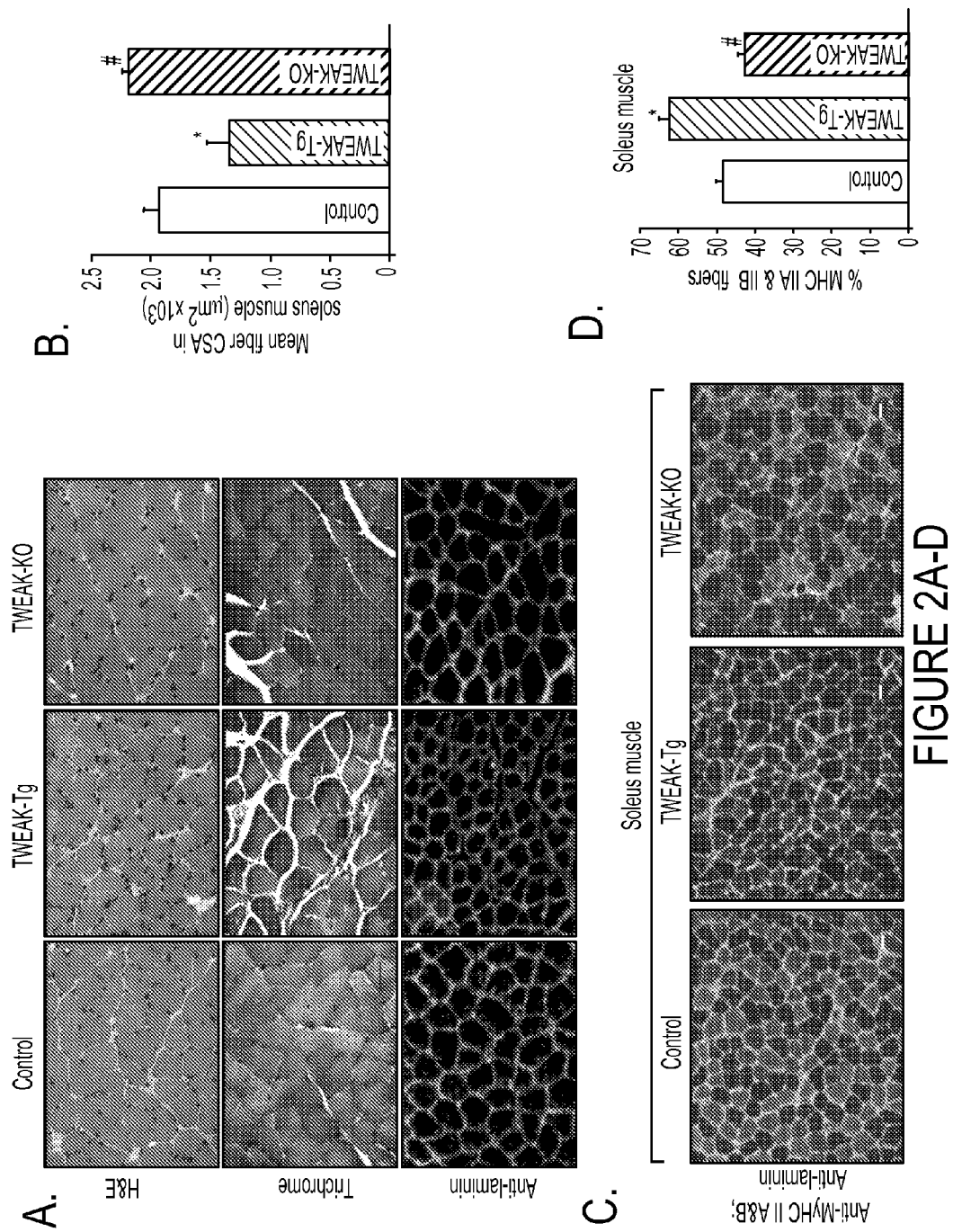
FIGURE 2A-D

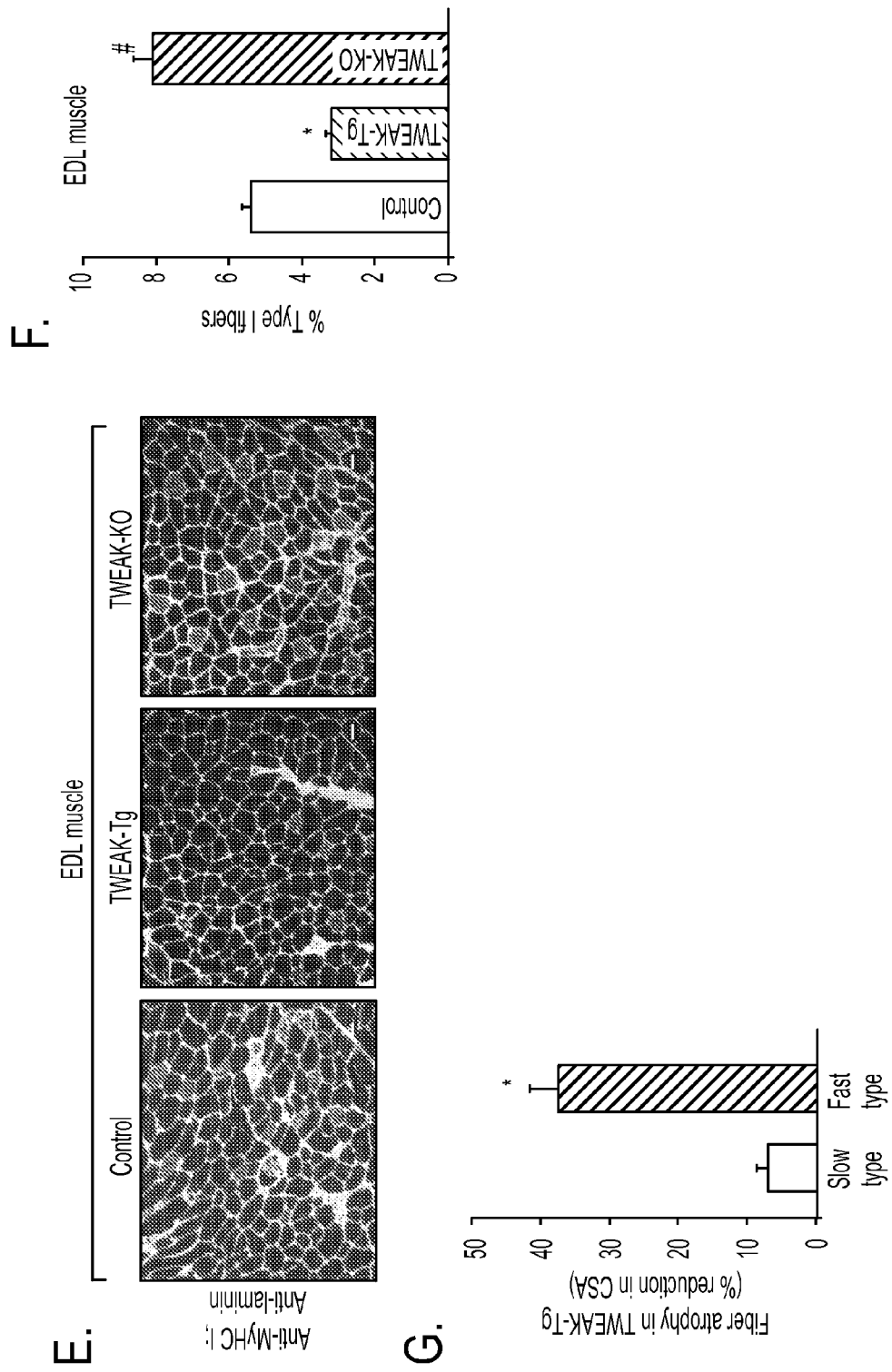
FIGURE 2E-G

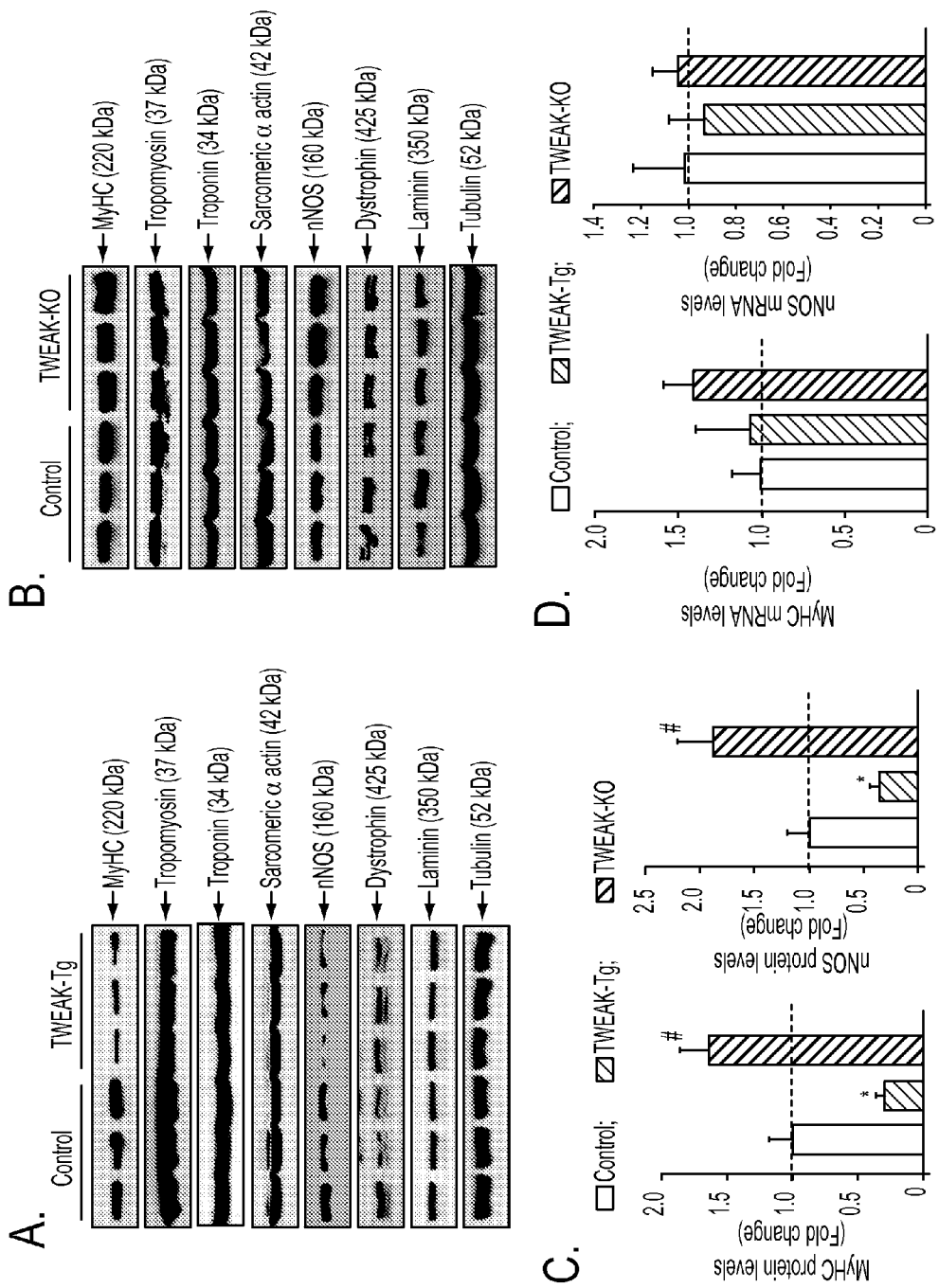
FIGURE 3A-D

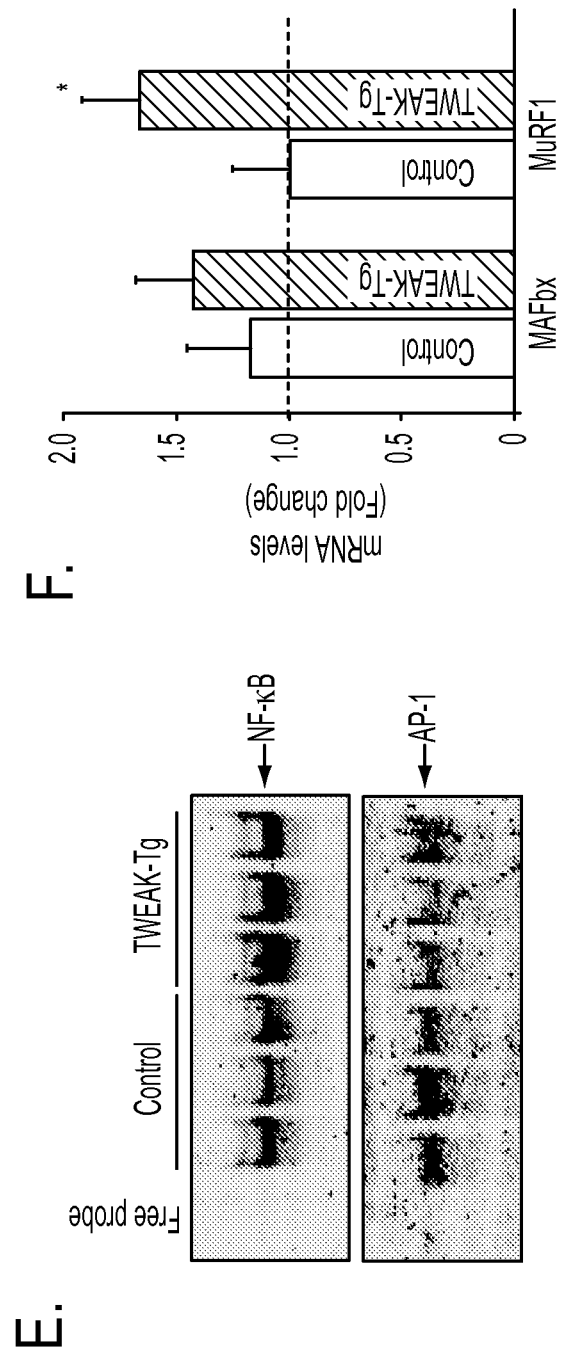
FIGURE 3E, F

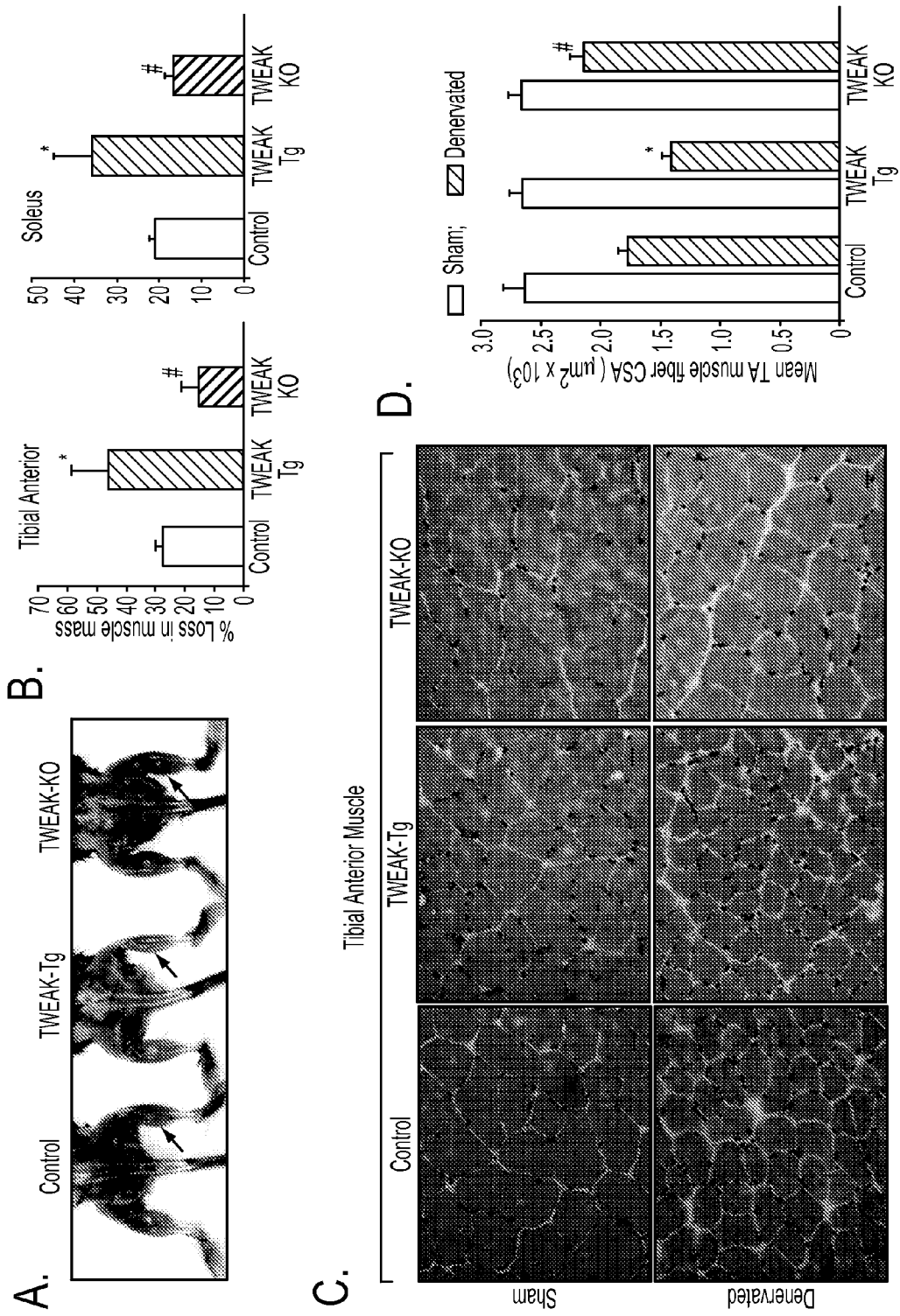
FIGURE 5A-D

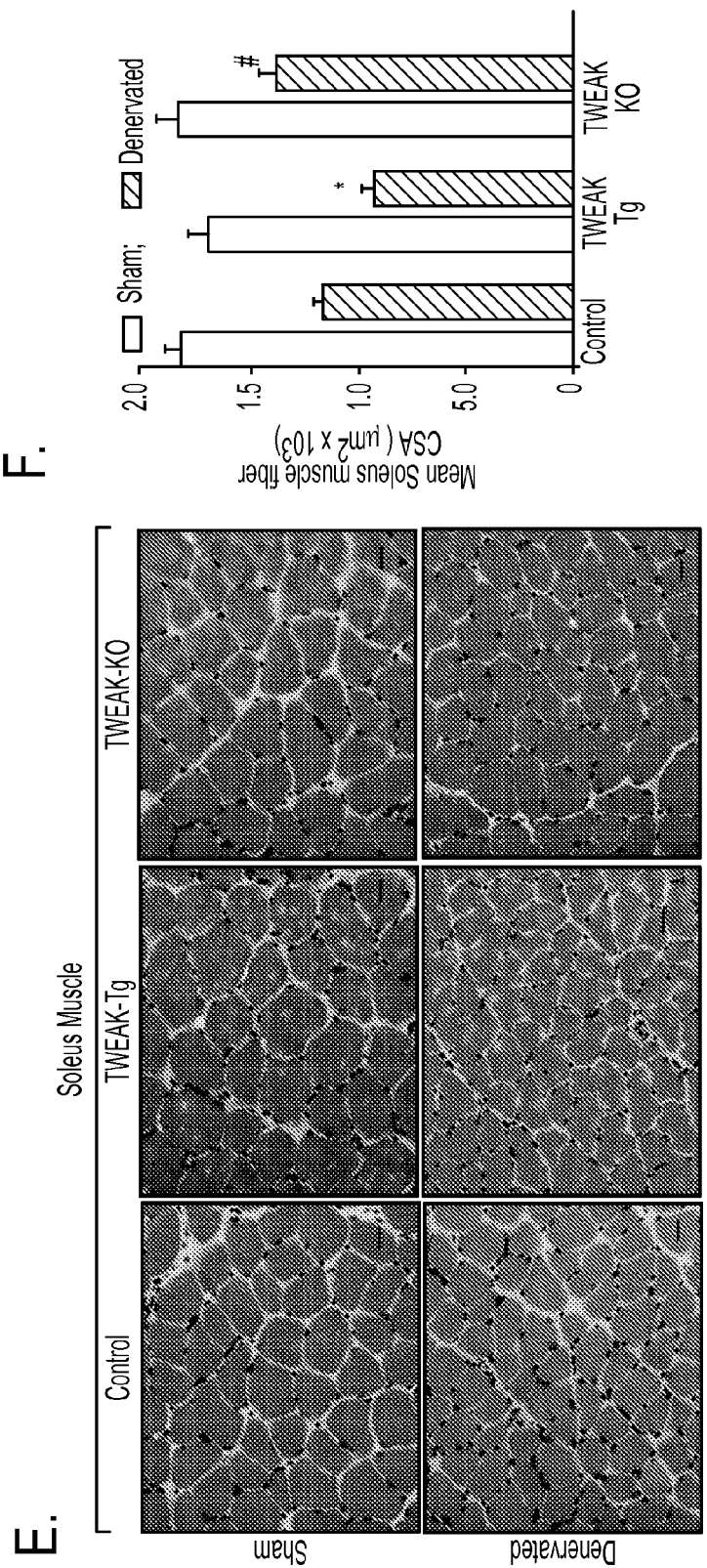
FIGURE 5 E,F

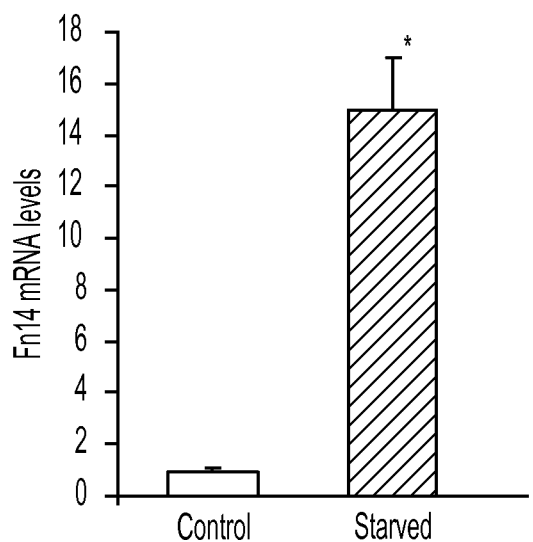
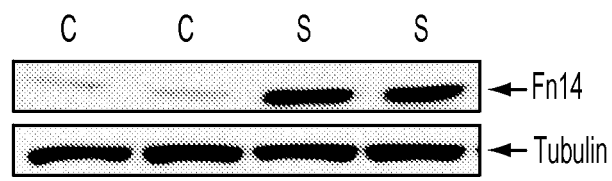
FIGURE 21

TWEAK/FN14 SYSTEM REGULATES SKELETAL MUSCLE ATROPHY AND REGENERATION

CROSS-REFERENCE TO RELATED APPLICATION(S)

This patent application claims the benefit of priority of U.S. application Ser. No. 61/301,454, filed Feb. 4, 2010, which application is herein incorporated by reference.

STATEMENT OF GOVERNMENT SUPPORT

This invention was made with government support under Grant #R01 AG129623 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Sep. 13, 2012, is named 175417US.txt and is 9,827 bytes in size.

BACKGROUND

Skeletal muscle undergoes atrophy characterized by a reduction in fiber cross-sectional area, protein content, and strength in several chronic conditions including cancer, diabetes, chronic obstructive pulmonary disease, chronic heart failure, cystic fibrosis, AIDS, anorexia, and after high dose treatment with glucocorticoids (see, e.g., Glass, *Nat Cell Biol.*, 5, 87-90 (2003) and Sandri, *Physiology (Bethesda)*, 23, 160-170 (2008)). Skeletal muscle also undergoes atrophy when its level of neuromuscular activity is reduced, for example, because of denervation, unloading, or immobilization (Jackman et al., *Am J Physiol Cell Physiol.*, 287, C834-43 (2004)) and due to "functional denervation", e.g., in elderly patient with sarcopenia (Macaluso et al., *Eur J Appl Physiol.*, 91, 450-472 (2004)). Furthermore, insufficient regeneration of skeletal muscle also causes the loss of skeletal muscle mass in diverse conditions, e.g., battle field or accidental injury (McKinnell et al., *Curr Top Dev Biol.* 71, 113-130 (2005)). However, little is known about the triggers and/or the molecular events leading to loss of skeletal muscle mass, e.g., in disuse conditions, injury, anorexia, or chronic disease states. Accordingly, identification of triggers and/or the molecular events leading to loss of skeletal muscle mass are needed, e.g., to identify physiological mechanisms for treating conditions associated with loss of skeletal muscle mass. Treatments for preventing loss of skeletal muscle, for preventing loss of force production and for augmenting skeletal muscle regeneration are needed.

SUMMARY OF CERTAIN EMBODIMENTS OF THE INVENTION

Certain embodiments of the present invention provide methods for preventing loss of skeletal muscle in a patient, comprising administering to a patient having a muscle disuse condition or injury, reduced caloric intake, or diabetes a therapeutically effective amount of an agent that decreases the activity of the TWEAK/Fn14 system so as to prevent the loss of skeletal muscle.

Certain embodiments of the present invention provide methods for preventing loss of force production by skeletal muscle in a patient, comprising administering to a patient having a muscle disuse condition or injury, reduced caloric intake, or diabetes a therapeutically effective amount of an agent that decreases the activity of the TWEAK/Fn14 system so as to prevent loss of force production by the skeletal muscle.

Certain embodiments of the present invention provide methods for augmenting skeletal muscle regeneration in a patient, comprising administering to a patient in need thereof a therapeutically effective amount of an agent that decreases the activity of the TWEAK/Fn14 system so as to augment skeletal muscle regeneration.

Certain embodiments of the present invention provide the use of an agent that decreases the activity of the TWEAK/Fn14 system for preventing the loss of skeletal muscle and/or loss of force production by skeletal muscle caused by sarcopenia, space flight, denervation, immobilization, cachexia, unloading, battlefield or accidental injury, reduced caloric intake or diabetes.

Certain embodiments of the present invention provide methods for preventing loss of skeletal muscle in a patient, comprising administering to a patient having a muscle disuse condition or injury a therapeutically effective amount of an agent that decreases the activity of the TWEAK/Fn14 system so as to prevent the loss of skeletal muscle.

In certain embodiments, the muscle disuse condition is sarcopenia, space flight, denervation, immobilization, cachexia or unloading.

In certain embodiments, the muscle disuse condition is not cachexia.

In certain embodiments, the muscle disuse condition is sarcopenia.

In certain embodiments, the muscle injury is a battlefield or accidental injury.

In certain embodiments, the agent is an antibody against TWEAK.

In certain embodiments, the agent is an antibody against Fn14.

In certain embodiments, the agent is an RNA interference molecule targeted against TWEAK.

In certain embodiments, the agent is an RNA interference molecule targeted against Fn14.

In certain embodiments, the RNA interference molecule is an siRNA molecule.

In certain embodiments, the agent is an Fn14 receptor antagonist.

In certain embodiments, the agent is recombinant Fn14 or an analog thereof.

In certain embodiments, the skeletal muscle is a soleus, tibial anteriors, gastrocnemius, EDL, diaphragm, biceps, triceps, quadriceps, facial, tongue, or abdominal muscle.

Certain embodiments of the present invention provide methods for promoting slow to fast-type fiber switching, comprising administering to a patient an effective amount of an agent that increases the activity of the TWEAK/Fn14 system so as to promote slow to fast-type fiber switching.

Certain embodiments of the present invention provide methods for decreasing slow to fast-type fiber switching, comprising administering to a patient a effective amount of an agent that decreases the activity of the TWEAK/Fn14 system so as to decrease slow to fast-type fiber switching.

Certain embodiments of the present invention provide methods for identifying agents useful for treating patients having a muscle disuse condition, comprising identifying agents that decrease the activity of the TWEAK/Fn14 system.

Certain embodiments of the present invention provide methods for identifying agents useful for promoting slow to fast-type fiber switching, comprising identifying agents that increase the activity of the TWEAK/Fn14 system.

Certain embodiments of the present invention provide methods for identifying agents useful for decreasing slow to fast-type fiber switching, comprising identifying agents that decrease the activity of the TWEAK/Fn14 system.

Certain embodiments of the present invention provide methods for augmenting skeletal muscle regeneration, e.g., after battlefield or accidental injury, comprising administering to a patient a therapeutically effective amount of an agent that decreases the activity of the TWEAK/Fn14 system so as to augmenting skeletal muscle regeneration.

Certain embodiments of the present invention provide the use of an agent that decreases the activity of the TWEAK/Fn14 system for preventing loss of skeletal muscle in a patient having a muscle disuse condition, anorexia, or diabetes (e.g., type II diabetes).

Certain embodiments of the present invention provide the use of an agent that decreases the activity of the TWEAK/Fn14 system for augmenting skeletal muscle regeneration, e.g., after battlefield or accidental injury.

BRIEF DESCRIPTION OF THE FIGURES

FIG. 2. Effect of TWEAK on skeletal muscle phenotypes in vivo. (A) Soleus muscle from 6-month old control (n=6), TWEAK-Tg (n=8) and TWEAK-KO (n=5) were analyzed after Hematoxylin and Eosin (H&E) or Masson's Trichrome staining or after immunostaining with laminin antibody. Scale bar: 50 μm (B) Quantification of average fiber cross-sectional area in soleus muscle of control, TWEAK-Tg, and TWEAK-KO mice. *p<0.01 and #p<0.05, value significantly different from control mice. (C) Representative photomicrographs of soleus muscle sections from 6-months old control (n=6), TWEAK-Tg (n=7) and TWEAK-KO (n=6) mice taken after immunostaining with anti-fMHC and anti-laminin. (D) Quantification of fMHC-positive and negative fibers in control, TWEAK-Tg, and TWEAK-KO mice *p<0.05, #p<0.05, values significantly different from control mice. (E) Representative photomicrographs of EDL muscle sections from 6-months old control (n=4), TWEAK-Tg (n=4) and TWEAK-KO (n=4) mice taken after immunostaining with anti-type I (clone: A4.840) and anti-laminin. (F) Percentage of type I (filled with red color) in control, TWEAK-Tg, and TWEAK-KO mice *p<0.05, #p<0.05, values significantly different from control mice. (G) Measurement of mean fiber cross-sectional area of fast-type and slow-type fibers in control (n=5) and TWEAK-Tg (n=5) mice revealed that TWEAK induces atrophy mainly in fast-type fibers. *p<0.01, value significantly difference from slow-type fibers.

FIG. 3. Effect of TWEAK on the expression of specific muscle proteins in vivo. (A) Representative immunoblots for MyHC, nNOS, tropomyosin, troponin, sarcomeric α actin, dystrophin, laminin, and tubulin in soleus muscle of 6 months old control and TWEAK-Tg mice. (B) Representative Western blots for various muscle proteins in soleus muscle of 6-months control and TWEAK-KO mice. (C) Fold change in protein levels of MyHC and nNOS in soleus muscle of control (n=6), TWEAK-Tg (n=5), and TWEAK-KO (n=6) mice. *$^{/\#}$p<0.05, values significantly different from control mice. (D) Fold change in mRNA level of MyHC and nNOS in soleus muscle of control (n=6), TWEAK-Tg (n=5), and TWEAK-KO (n=4) mice. (E) Activation of NF-κB but not AP-1 transcription factor in soleus muscle of 6 months old TWEAK-Tg compared to littermate control mice. (F) Fold difference in mRNA levels of MAFBx and MuRF1 in control and TWEAK-Tg mice. *p<0.01, values significantly different from level of MuRF1 in control mice.

FIG. 5. Role of TWEAK in denervation-induced skeletal muscle atrophy. (A). Three months old control, TWEAK-Tg and TWEAK-KO mice 10 days after denervation procedure. Arrow points to denervated gastrocnemius muscle. (B) Tibial anterior (TA) and soleus muscle were isolated from tendon to tendon from control, TWEAK-Tg, and TWEAK-KO mice 10 days after denervation (n=6 per group) and their wet weight was measured. *p<0.05, #p<0.05, values significantly different from corresponding muscle of control mice. (C) Hematoxylin and Eosin (H&E) stained sections of tibial anterior (TA) of control, TWEAK-Tg, TWEAK-KO mice 10 days after denervation. Scale bar: 20 μm (D) Quantification of fiber cross-sectional area (CSA) of TA muscle in control, TWEAK-Tg and TWEAK-KO mice 10 days after denervation (n=8 in each group). *p<0.01 and #p<0.05, values significantly different from that of control mice at indicated time after denervation. (E). Representative photomicrographs of H&E-stained soleus muscle sections from control, TWEAK-Tg, TWEAK-KO mice 12 days after denervation. Scale bar: 20 μm. (F). Measurement of fiber CSA in H&E-stained soleus muscle sections in control, TWEAK-Tg, and TWEAK-KO mice 12 days after denervation (n=6 in each group). *p<0.01 and #p<0.05, values significantly different from that of control mice at indicated time after denervation.

FIG. 21. Expression of Fn14 in skeletal muscle of mice in response to starvation. C57BL6 mice were kept in normal conditions and food deprived for 24 h. Tibial anterior (TA) muscle isolated was used to study the Fn14 mRNA and protein levels. (A) Relative mRNA levels of Fn14 in TA muscle of control and 24 h-fasted mice (n=3 in each group). *p<0.05, values significantly different from unstarved (control) mice. Bars represent standard deviation (SD). (B) Representative immunoblots showing elevated protein level of Fn14 in TA muscle of starved mice. The level of an unrelated protein tubulin remained same in TA muscle of control or starved mice.

DETAILED DESCRIPTION

Figure 1:
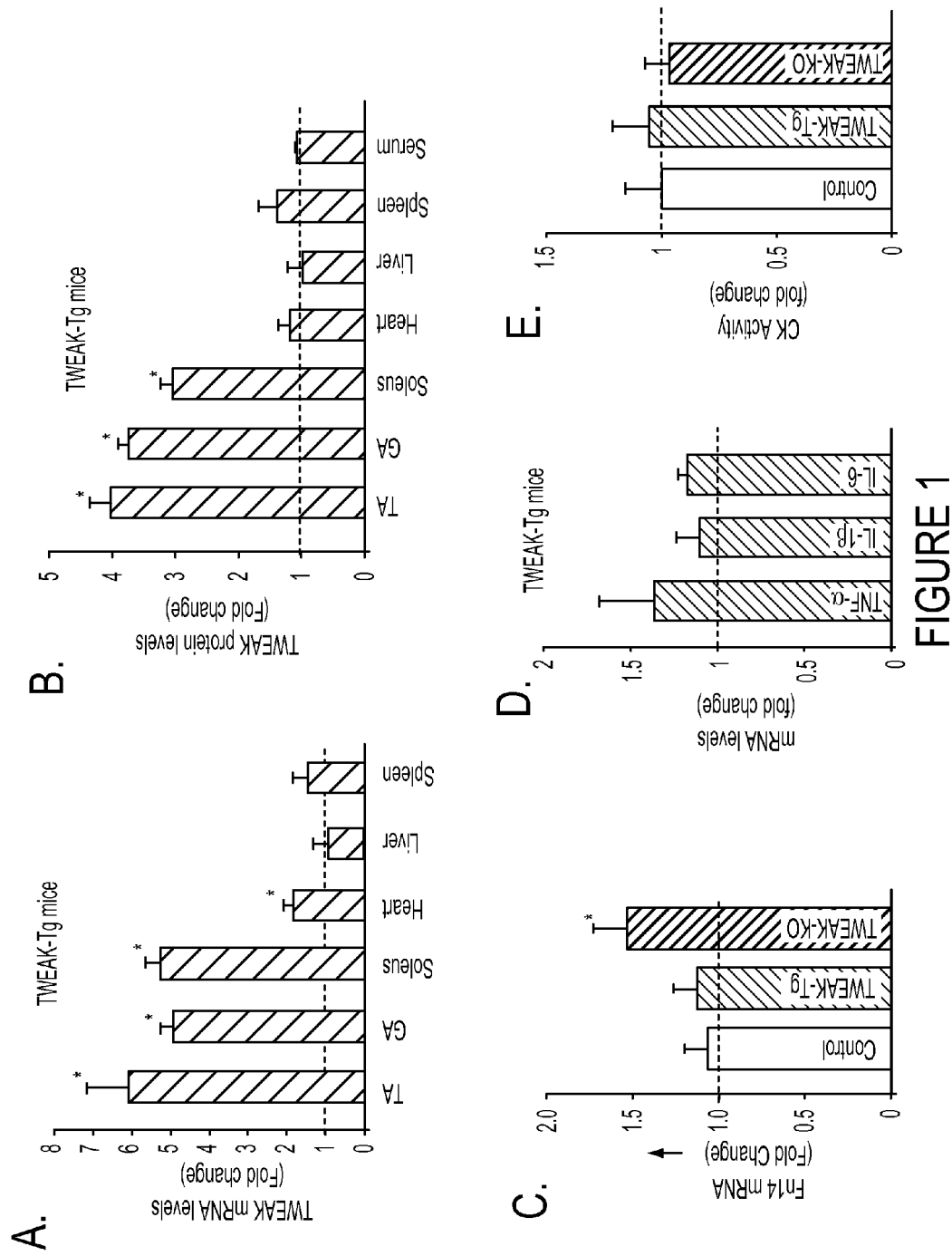
FIG. 1. Characterization of TWEAK-transgenic (Tg) and TWEAK-knockout (KO) mice. (A) Fold increase in mRNA levels of TWEAK in skeletal muscle and other organs of TWEAK-Tg mice (n=6) compared to littermate control (n=6) mice. *p<0.01, values significantly different from littermate control mice. (B). Fold change in protein levels of TWEAK in skeletal muscle, other tissues, and serum of TWEAK-Tg (n=3) mice compared to control (n=3) mice. *p<0.01, values significantly different from littermate control mice. (C) Fold change in the mRNA levels of TWEAK receptor in TA muscle of TWEAK-Tg (n=5) and TWEAK-KO (n=6) mice compared to control (n=6) mice. *p<0.01, values significantly different from age-matched wild-type mice. (D) Fold change in mRNA levels of TNF-α, IL-β, and IL-6 in TA muscle of TWEAK-Tg (n=3) mice compared to control mice (n=3). (E) Serum creatine kinase levels in TWEAK-Tg or TWEAK-KO mice compared to control mice measured using a creatine kinase assay kit (Stanbio Laboratory). TA, Tibial anterior; GA, gastrocnemius.

Skeletal muscle atrophy occurs in a variety of clinical settings, including disuse atrophy and denervation. As described herein, it has been discovered that the cytokine TWEAK and its receptor Fn14 mediates skeletal muscle atrophy in response to denervation. Transgenic expression of TWEAK induced atrophy, fibrosis, fiber-type switching, and the degradation of muscle proteins. Conversely, genetic ablation of TWEAK decreased the loss of muscle proteins and spared fiber cross-sectional area, muscle mass and strength after denervation. Expression of the TWEAK receptor Fn14 was significantly increased in muscle upon denervation, demonstrating an unexpected "inside-out" signaling pathway leading to atrophy. TWEAK activates NF-$\kappa$B, causing an increase in the expression of the E3 ubiquitin ligase MuRF1. Accordingly, the TWEAK/Fn14 system is an important target for preventing skeletal muscle wasting. Further, increased expression of Fn14 was also observed in skeletal muscle in response to immobilization and unloading, events in which there has not been nerve injury. This provides the first evidence that the levels of Fn14 are increased in skeletal muscle in three disuse conditions (i.e., denervation, immobilization, and unloading).

The physiological significance of TWEAK in skeletal muscle, and the mechanisms by which TWEAK induces skeletal muscle wasting in vivo, are currently unknown. As described herein, it has been demonstrated that constitutive overexpression of TWEAK causes significant muscular abnormalities that are reminiscent of skeletal muscle wasting in chronic diseases. Further, it has been demonstrated that TWEAK is an important mediator of skeletal muscle atrophy in response to denervation. Transgenic overexpression of TWEAK in skeletal muscle exacerbates atrophy, whereas genetic ablation of TWEAK rescues the loss of skeletal muscle mass and strength after denervation. It has also been discovered that TWEAK functions through the activation of NF-$\kappa$B and by stimulating the expression of the E3 ubiquitin ligase MuRF-1 in denervated skeletal muscle.

Certain embodiments of the present invention provide methods for preventing loss of skeletal muscle in a patient, comprising administering to a patient having a muscle disuse condition or injury, reduced caloric intake, or diabetes a therapeutically effective amount of an agent that decreases the activity of the TWEAK/Fn14 system so as to prevent the loss of skeletal muscle.

Certain embodiments of the present invention provide methods for preventing loss of force production by skeletal muscle in a patient, comprising administering to a patient having a muscle disuse condition or injury, reduced caloric intake, or diabetes a therapeutically effective amount of an agent that decreases the activity of the TWEAK/Fn14 system so as to prevent loss of force production by the skeletal muscle.

Certain embodiments of the present invention provide methods for augmenting skeletal muscle regeneration in a patient, comprising administering to a patient in need thereof a therapeutically effective amount of an agent that decreases the activity of the TWEAK/Fn14 system so as to augment skeletal muscle regeneration.

In certain embodiments, the patient has a muscle disuse condition or injury.

In certain embodiments, the muscle disuse condition is sarcopenia, space flight, denervation, immobilization, cachexia or unloading.

In certain embodiments, the muscle disuse condition is sarcopenia.

In certain embodiments, the patient does not have cachexia.

In certain embodiments, the muscle injury is a battlefield or accidental injury.

In certain embodiments, the patient has reduced caloric intake or diabetes.

In certain embodiments, the patient has reduced caloric intake.

In certain embodiments, the patient having the reduced caloric intake is a patient with cancer.

In certain embodiments, the patient having the reduced caloric intake is a patient with anorexia.

In certain embodiments, the patient has diabetes.

In certain embodiments, the patient has type II diabetes.

In certain embodiments, the agent is an antibody against TWEAK.

In certain embodiments, the agent is an antibody against Fn14.

In certain embodiments, the agent is an RNA interference molecule targeted against TWEAK.

In certain embodiments, the agent is an RNA interference molecule targeted against Fn14.

In certain embodiments, the RNA interference molecule is an siRNA molecule.

In certain embodiments, the agent is an Fn14 receptor antagonist.

In certain embodiments, the agent is recombinant Fn14 or an analog thereof.

In certain embodiments, the skeletal muscle is a soleus, tibial anteriors, gastrocnemius, EDL, diaphragm, biceps, triceps, quadriceps, facial, tongue, or abdominal muscle.

In certain embodiments, the administration of the therapeutically effective amount of an agent that decreases the activity of the TWEAK/Fn14 system prevents the loss of force production by the skeletal muscle.

In certain embodiments, the administration of the therapeutically effective amount of an agent that decreases the activity of the TWEAK/Fn14 system augments skeletal muscle regeneration.

Certain embodiments of the present invention provide methods for promoting slow to fast-type fiber switching, comprising administering to a patient an effective amount of an agent that increases the activity of the TWEAK/Fn14 system so as to promote slow to fast-type fiber switching.

Certain embodiments of the present invention provide methods for decreasing slow to fast-type fiber switching, comprising administering to a patient a effective amount of an agent that decreases the activity of the TWEAK/Fn14 system so as to decrease slow to fast-type fiber switching.

Certain embodiments of the present invention provide methods for identifying agents useful for treating patients having a muscle disuse condition or injury, comprising identifying agents that decrease the activity of the TWEAK/Fn14 system.

Certain embodiments of the present invention provide methods for identifying agents useful for promoting slow to fast-type fiber switching, comprising identifying agents that increase the activity of the TWEAK/Fn14 system.

Certain embodiments of the present invention provide methods for identifying agents useful for decreasing slow to fast-type fiber switching, comprising identifying agents that decrease the activity of the TWEAK/Fn14 system.

Certain embodiments of the present invention provide the use of an agent that decreases the activity of the TWEAK/Fn14 system for preventing loss of skeletal muscle in a patient having a muscle disuse condition.

Certain embodiments of the present invention provide the use of an agent that decreases the activity of the TWEAK/Fn14 system for preventing loss of force production by skeletal muscle in a patient.

Certain embodiments of the present invention provide the use of an agent that decreases the activity of the TWEAK/Fn14 system for augmenting skeletal muscle regeneration.

Certain embodiments of the present invention provide the use of an agent that decreases the activity of the TWEAK/Fn14 system for treating diabetes.

Certain embodiments of the present invention provide the use of an agent that decreases the activity of the TWEAK/Fn14 system for treating reduced caloric intake, caused by, e.g., cancer or anorexia.

Certain embodiments of the present invention provide the use of an agent that decreases the activity of the TWEAK/Fn14 system for preventing the loss of skeletal muscle and/or loss of force production by skeletal muscle caused by sarcopenia, space flight, denervation, immobilization, cachexia, unloading, battlefield or accidental injury, reduced caloric intake or diabetes.

Agent that decreases the activity of the TWEAK/Fn14 system are known in the art. For example, antibodies against TWEAK and Fn14 are known in the art, as are methods of generating and screening for antibodies against TWEAK and Fn14. For example, please refer to the following U.S. Patent and U.S. Patent Publications Numbers for agent that decreases the activity of the TWEAK/Fn14 system: 2010/0255008, 2008/0241163, 2009/0137036, U.S. Pat. Nos. 7,732,588, 7,169,387, 7,579,001, 2007/0110745, 2010/0061985, 2009/0324602, 2010/0284933, 2009/0068102, 2009/0311313, 2009/0124993, 2010/0272721, 2008/0187544 and 2006/0003932.

The term "starvation", as used herein, refers to a condition of reduced caloric intake, which reduction would typically cause loss of skeletal muscle and/or loss of force production by the skeletal muscle. Such a reduction of caloric intake may be caused by, e.g., anorexia or cancer.

The invention will now be illustrated by the following non-limiting Examples.

EXAMPLE 1

Skeletal muscle atrophy is commonly observed in disuse conditions such as denervation, unloading, and immobilization. Proinflammatory cytokines have been suggested both to induce and mediate local catabolic mechanisms at advance stages of chronic diseases leading to cachexia. However, since disuse-related skeletal muscle atrophy does not involve any systematic inflammatory response, the involvement of proinflammatory cytokines in this type of atrophy has received limited attention. Furthermore, studies investigating the roles of proinflammatory cytokine in disuse atrophy have generally focused on classical muscle-wasting cytokines such as TNF-α, IL-1β, IL-6, and IFN-γ. Gene expression studies have found no evidence for the involvement of these cytokines in disuse-related muscle atrophy (see, e.g., Bodin et al., *Science*, 294, 1704-1708 (2001), Gomes et al., PNAS, 98, 14440-14445 (2001) and Stevenson et al., *J Physiol.*, 551, 33-48 (2003)). The results of the research described herein provides strong evidence, for the first time, that the inflammatory cytokine TWEAK is an important mediator of denervation-induced skeletal muscle atrophy.

Over-expression of TWEAK is Sufficient to Cause Atrophy and an Upregulation of NF-κB/MuRF1-Induced Protein Degradation.

Transgenic mice were produced in which TWEAK was over-expressed 4-6 fold (FIG. 2A, B). These animals live into adulthood. This is in contrast to prior TWEAK transgenics, in which the cytokine was expressed at 14-fold normal levels. Those animals died at peri- or neonatally, due to excessive muscle loss (Dogra et al. *FASEB J.*, 21, 1857-1869 (2007)).

Figure 6:
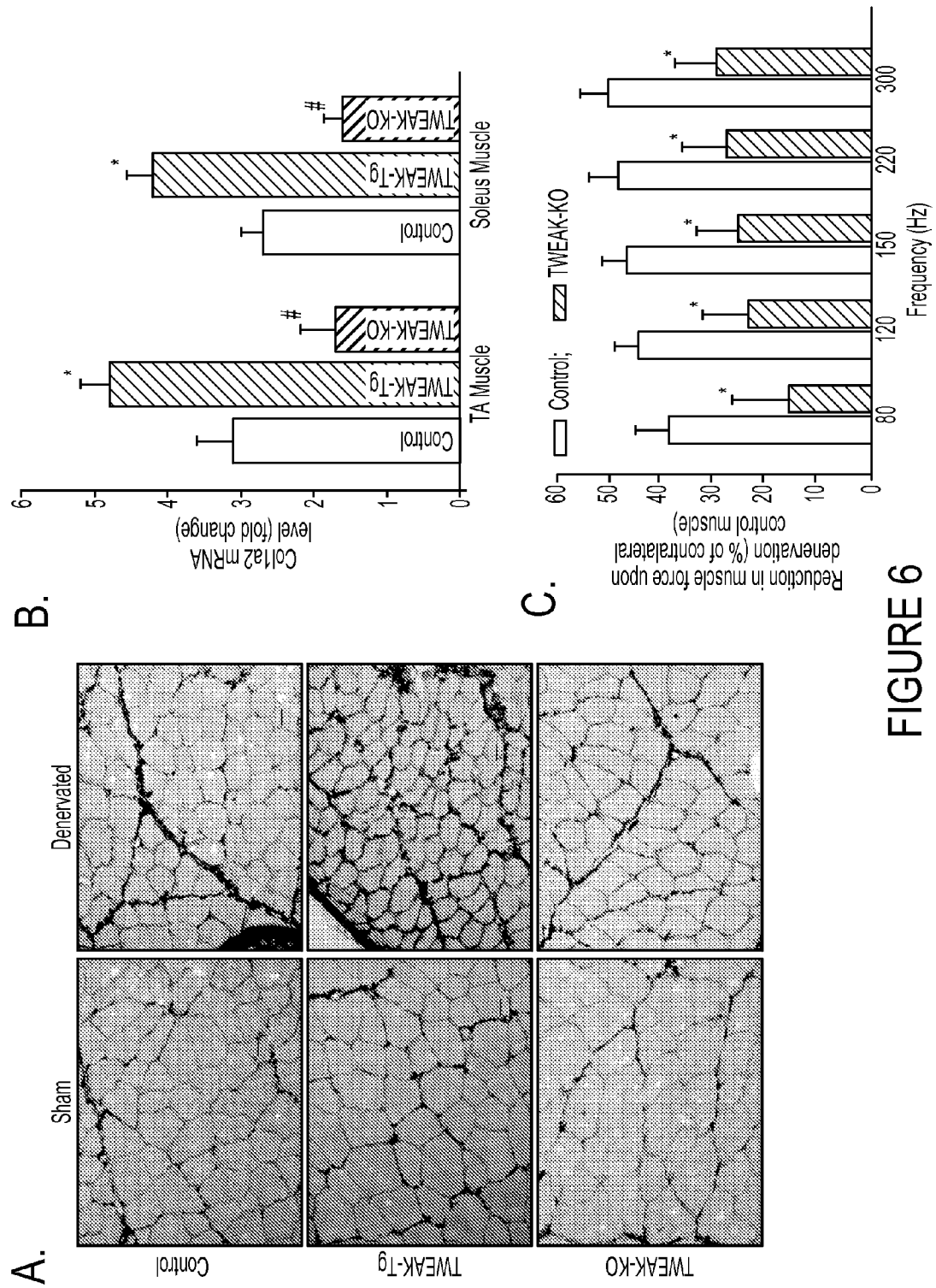
FIG. 6. Role of TWEAK in Development of fibrosis and loss of muscle function. (A) Sirius red staining performed on TA muscle sections after 21 days of denervation in control, TWEAK-Tg and TWEAK-KO mice (n=4 in each group). (B) Fold change in the mRNA levels of collagen type 1, alpha 2 (Col1a2) in control (n=6), TWEAK-Tg (n=3) and TWEAK-KO (n=3) in TA and soleus muscle 10 days after denervation measured by QRT-PCR. *$p<0.01$, values significantly different from denervated muscle of control mice. (C) Denervation-induced loss in absolute muscle force production in isometric contraction was measured in soleus muscle of control (n=5) and TWEAK-KO (n=6) mice at 80, 120, 150, 220 and 300 Hz. *$p<0.01$, values significantly different from the denervated soleus muscle of control mice at same frequency.

Transgenic mice over-expressing TWEAK 4- to 6-fold show no gross phenotype until the animals are around six months of age. At that time, a decrease in muscle fiber size can be observed, coincident with an increase in fibrosis. This is a similar phenotype to that seen in settings of denervation (FIG. 2A and FIGS. 6 A and B). Coincident with the onset of atrophy, there is an increase in the activity of NF-κB transcription factor (FIG. 3E) and the levels of the E3 ubiquitin ligase MuRF1 (FIG. 3F), but not those of a second muscle-specific E3 ligase, MAFbx. MuRF1 and MAFbx are found to be co-activated in many settings of muscle atrophy. However it was also previously demonstrated that discrete activation of the NF-κB pathway induces MuRF1 but not MAFbx expression, placing MuRF1 downstream of NF-kappaB; MAFbx can be activated by p38 signaling.

MuRF1 is a specific E3 ligase for Myosin Heavy Chain (MyHC) protein. It degrades MyHC, and other components of the thick filament, such as myosin light chain. The loss of MyHC in the six-month old TWEAK-Tg animals (FIG. 3A) indicates that the MuRF1/MyHC pathway has been activated by TWEAK/FN14 signaling, demonstrating a TWEAK/FN14/NF-kB/MuRF1/MyHC protein degradation cascade.

It is of interest that otherwise-unperturbed TWEAK-transgenic (Tg) animals did not display a phenotype until they were older. This suggests the possibility that a second, age-dependent, event occurs in order for TWEAK overexpression to be sufficient to induce atrophy. The late appearance of atrophic phenotype in TWEAK-Tg mice (i.e., after 4 months) suggest that the catabolic action of TWEAK in skeletal muscle may be neutralized by active muscle formation and/or the presence of growth factors at a younger age. It is also possible that TWEAK has different roles in the acquisition and the maintenance of skeletal muscle mass in vivo. An increased concentration of TWEAK induces interstitial fibrosis in skeletal muscle (FIG. 2A). The increased number of type II fibers in soleus muscle of TWEAK-Tg mice also indicate that the elevated levels of TWEAK are sufficient to induce transition of slow-type fibers into fast-type and its absence increases the proportion of slow-type fibers (FIGS. 3C-F). The results indicate that proinflammatory cytokines and chronic diseases favor a switch from type I (slow twitch) to type II (fast twitch) fibers and that muscle atrophy occurs primarily in fast twitch fibers (FIG. 3G) in atrophying conditions.

While it is of interest to show that ectopic, enhanced expression of TWEAK is sufficient to induce skeletal muscle atrophy, that finding by itself does not explain what happens under "normal" settings of atrophy. Therefore, it was interesting to see that genetic ablation of TWEAK augments fiber cross-sectional area. This finding demonstrates that TWEAK is a negative regulator of skeletal muscle mass in adult animals (FIGS. 2 A, B).

Skeletal muscle wasting can result due to enhanced protein degradation or reduced protein synthesis or both (Glass, *Int J Biochem Cell Biol.*, 37, 1974-1984 (2005)). Recent evidence suggests that muscle-wasting in response to cancer cachexia involve the degradation of only selective muscle proteins. For example, Acharyya has reported that cancer cachexia also involves sarcolemmal abnormalities including the reduced expressions of the components of dystrophin-glycoprotein complex (DGC) in skeletal muscle (Acharyya et al., *Cancer Cell.*, 8, 421-432 (2005)). As demonstrated herein, skeletal muscle atrophy in TWEAK-Tg is associated with reduced levels of contractile proteins MyHC and tropomyosin (FIG. 3A,C). Furthermore, the level of neural nitric oxide synthase (nNOS), a protein which interacts with DGC in skeletal muscle, but not dystrophin and laminin is reduced in TWEAK-Tg mice (FIG. 3A). These results indicate that the increased levels of TWEAK may destabilize the sarcolemma in part by reducing the level of nNOS, thus disturbing the equilibrium and resulting in atrophy, and by upregulating NF-κB/MuRF1 signaling, causing actual breakdown of the thick filament.

Genetic Ablation of TWEAK Spares Skeletal Muscle under Denervation Conditions

Figure 7:
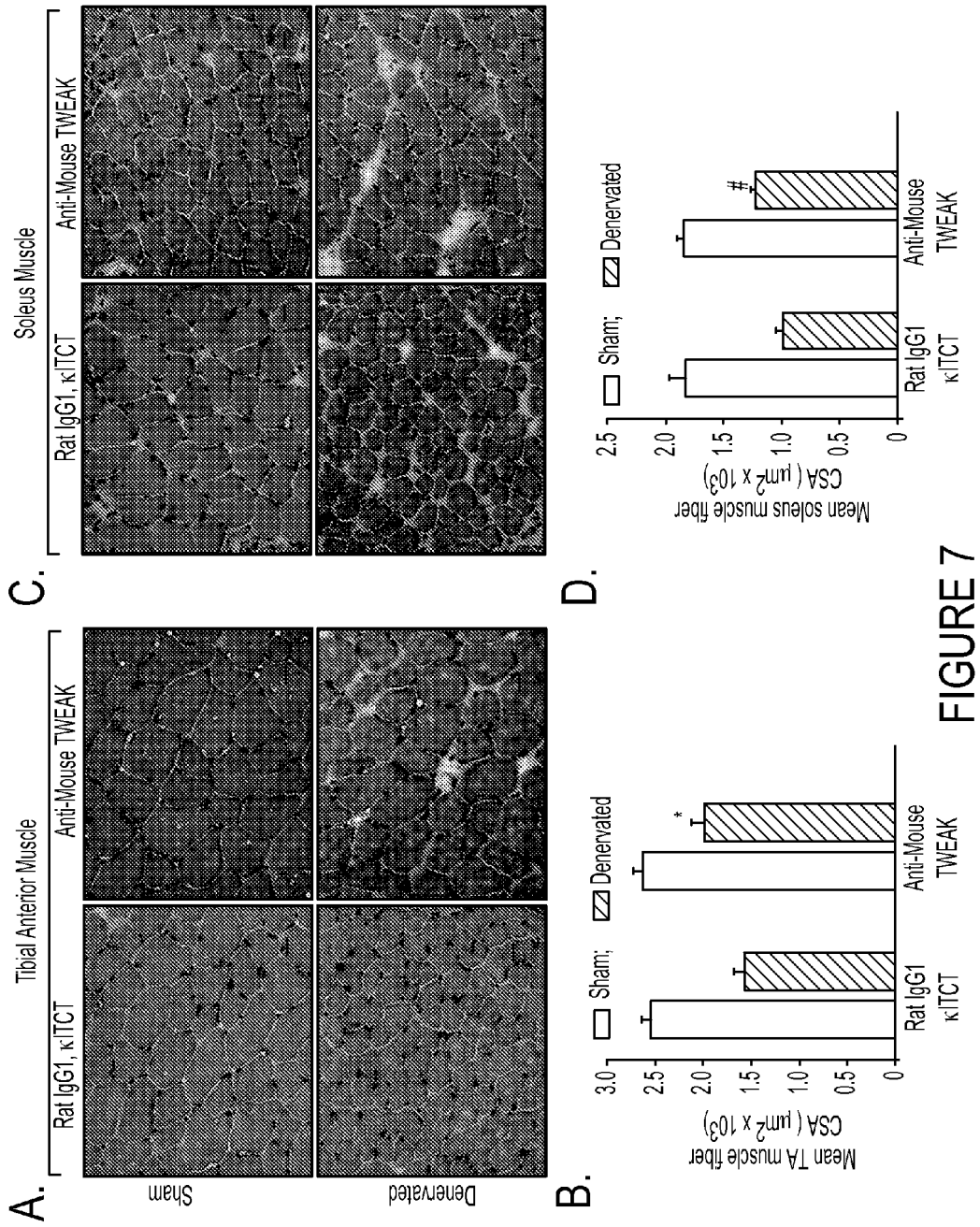
FIG. 7. TWEAK neutralizing antibody inhibits denervation-induced muscle loss in mice. Two months old C57BL6 mice were denervated for two days followed by intraperitoneal injections of 200 μg/mouse of either rat IgG1 or anti-TWEAK every third day for 12 days (n=4 in each group). (A). Representative photomicrographs of H&E-stained sections of control and denervated tibial anterior (TA) muscle of isotype and anti-TWEAK treated mice. Scale bar: 20 μm. (B). Quantification of fiber cross-sectional area (CSA) in TA muscle sections of isotype and anti-TWEAK treated mice. *$p<0.01$, values significantly different from denervated TA muscle of IgG1-treated mice. (C). H&E-stained sections of control and denervated soleus muscle of mice treated with isotype or anti-TWEAK. Scale bar: 20 μm. (D). Quantification of fiber CSA in soleus muscle sections. #$p<0.05$, values significantly different from denervated soleus muscle of IgG1-treated mice. ITCT, isotype control.

Although the underpinning mechanisms leading to the increased expression of Fn14 remains unknown, the present study demonstrates that the activation of TWEAK/Fn14 pathway mediates the loss of skeletal muscle mass and strength upon denervation (FIGS. 5, 6C, and 7). Additionally, increased fibrosis in the denervated muscle of the TWEAK-Tg mice further supports the contention that TWEAK is a major regulator of fibrosis in atrophying conditions (FIG. 6A, B).

Figure 8:
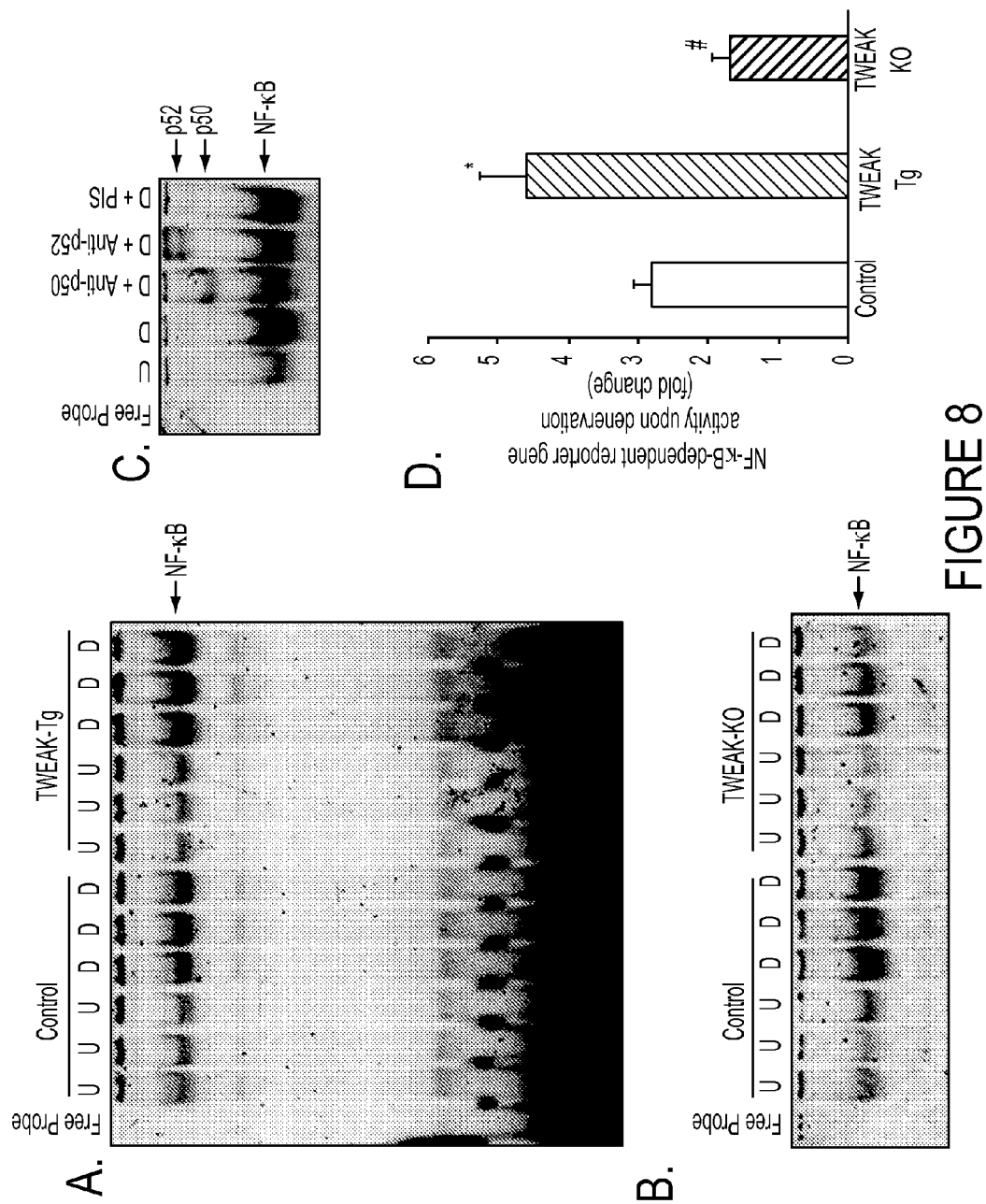
FIG. 8. Role of TWEAK in the activation of NF-κB in denervated skeletal muscles. DNA-binding activity of NF-κB was measured by EMSA in Tibial anterior (TA) muscle 10 days after denervation. Representative EMSA gel from three independent experiments for (A) control and TWEAK-Tg mice and (B) control and TWEAK-KO mice. (C) Supershift assay performed using nuclear extracts from denervated gastrocnemius muscle of control mice using antibodies against p50 and p52 subunits of NF-κB. PIS, pre-immune serum. (D) Fold change in NF-κB reporter gene activity (normalized using Renilla luciferase) in TA muscle of control, TWEAK-Tg, and TWEAK-KO mice after denervation. *$p<0.01$, #$p<0.05$, values significantly different from corresponding control mice. U, undenervated; D, denervated.

The loss of skeletal muscle proteins in atrophying muscle is mediated by the activation of the ATP-dependent ubiquitin-proteasome pathway, with an associated increase in the expression of the E3 ubiquitin ligases MAFbx and MuRF1. Prior to this study, the identity of particular upstream triggers of atrophy in the various models remained unknown. The results presented here demonstrate that the activation of TWEAK/Fn14 system specifically activates NF-κB in denervated muscle (FIG. 8). Although skeletal muscle-wasting might involve coordinated activation of multiple cell signaling pathways, NF-κB activation in skeletal muscle is sufficient to cause skeletal muscle wasting (Cai et al., *Cell*, 119, 285-298 (2004) and Li et al., *J. Mol. Med.*, 86, 1113-1126 (2008)), in part by activating MuRF1, since muscle-wasting in IKKβ-overexpressing transgenic mice was significantly reduced by crossing them with MuRF1-knockout mice. Furthermore, skeletal muscle-specific deletion of IKKβ in mice reduces the expression of MuRF1 gene and atrophy in response to denervation.

While MAFbx (also known as Atrogin-1) was activated by denervation in these studies (FIG. 8), this E3 ligase was not further perturbed by addition or deletion of TWEAK, adding evidence that NF-κB activation does not upregulate MAFbx expression.

Figure 12:
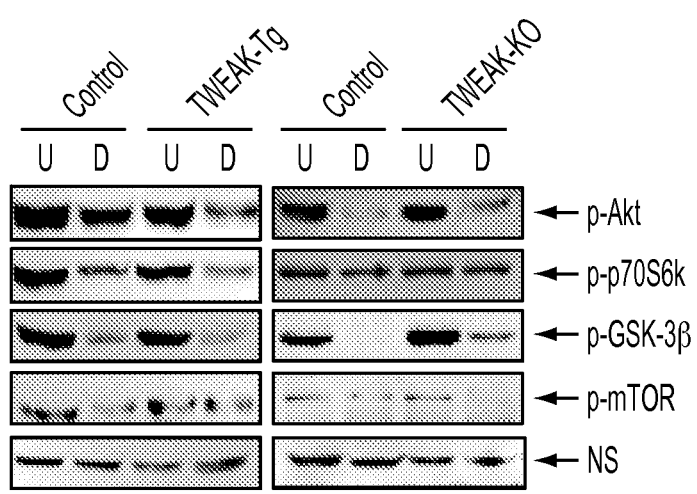
FIG. 12. Activation of Akt pathway in denervated skeletal muscle. Protein levels of phosphorylated Akt, p70S6K, mTOR, and GSK3β in denervated gastrocnemius muscle of control, TWEAK-Tg or TWEAK-KO mice were measured using western blot, incubating in indicated antibodies U, undenervated control; D, denervated.

It is also of interest to note some of the pathways that TWEAK did not activate. While TWEAK was found to stimulate NF-κB pathway, it did not affect the activation of Akt signaling pathway in denervated skeletal muscle (FIG. 12). While increased expression of several autophagy-related genes was observed in denervated skeletal muscle, there was no difference in their expression in denervated skeletal muscle of TWEAK-Tg or knockout mice (FIG. 13), and TWEAK overexpression was not sufficient to activate autophagy. Taken together, our results suggest that TWEAK/Fn14 pathway specifically upregulates the expression of the components of the ubiquitin-proteasome system (e.g., MuRF1) in denervated skeletal muscle.

The TWEAK/FN14 Pathway Provides a Novel Signaling Mechanism to Regulate Skeletal Muscle Mass under Denervation Conditions The data presented herein demonstrates a previously undiscovered and surprising mechanism for modulating skeletal muscle atrophy. The fact that the Fn14 receptor, but not TWEAK itself, is upregulated under atrophy conditions suggests a mechanism in which muscle creates a "permissive" setting for atrophy by modulating the TWEAK receptor. Since TWEAK itself is not perturbed, the data suggests that the receptor's expression is limiting for TWEAK to function. It is noteworthy that in younger animals TWEAK overexpression is not sufficient to cause atrophy, but it is able to increase muscle loss under atrophy conditions. Since the TWEAK receptor Fn14 is upregulated by denervation, this adds further data for the inference that Fn14 levels are limiting, and therefore TWEAK requires FN14 upregulation in order to induce atrophy.

Figure 15:
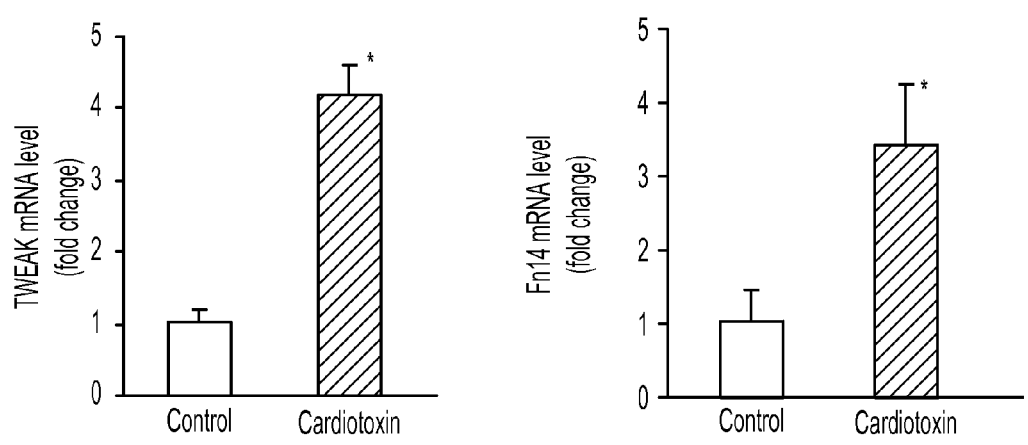
FIG. 15. Expression of TWEAK and Fn14 are increased in skeletal muscle in response to injury. Tibial anterior (TA) muscles of wild-type (wt) mice were given intramuscular injection of either saline or cardiotoxin. After five days, the expression of TWEAK and Fn14 was studied by quantitative real-time PCR (QRT-PCR) method. Data presented here show that the expression of both TWEAK and its receptor Fn14 are significantly increased in cardiotoxin-injected TA muscle providing initial evidence that this ligand-receptor dyad may play a role in skeletal muscle regeneration. *$p<0.01$, values significantly different from corresponding TA muscle injected with saline alone.
Figure 16A:
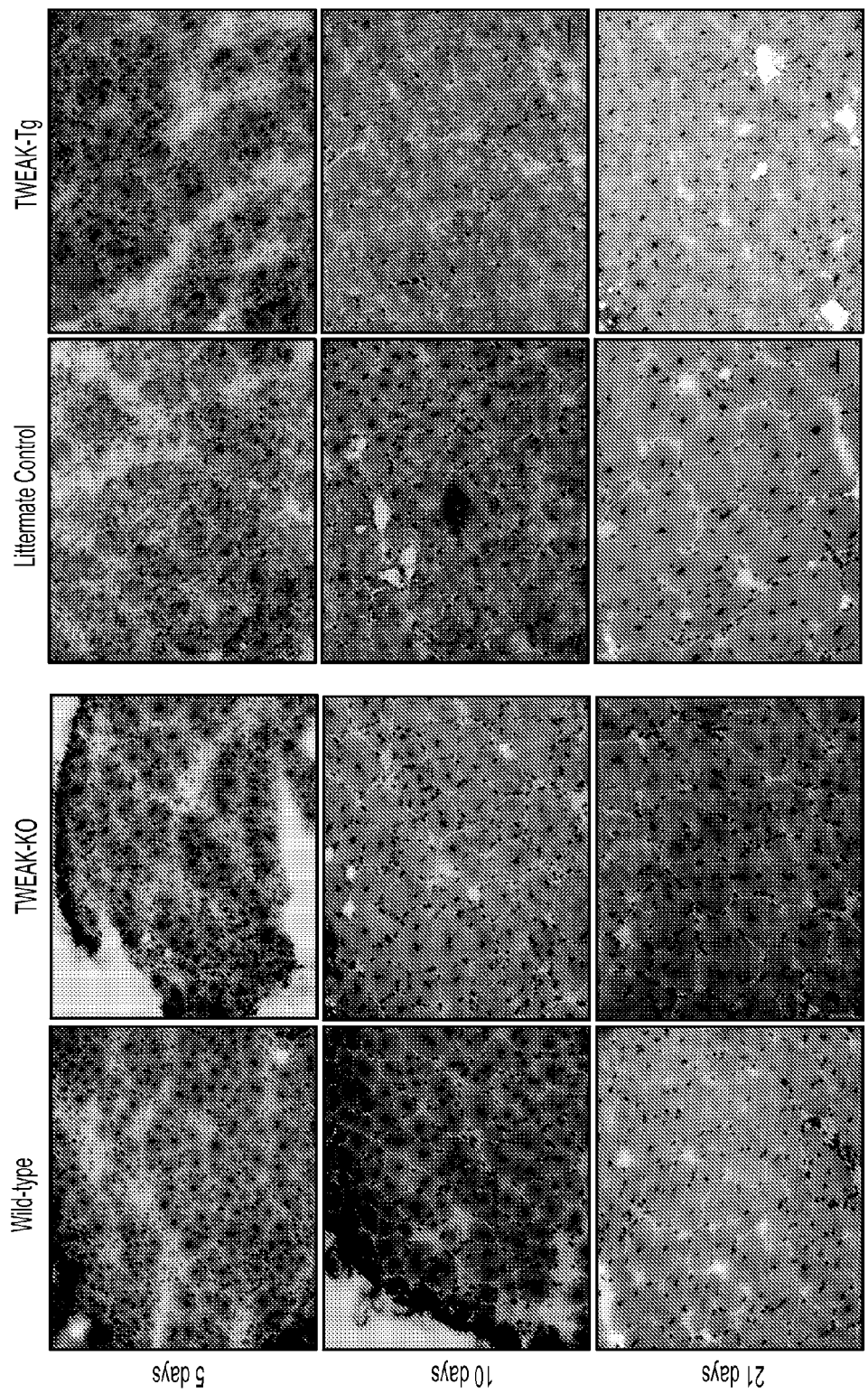
FIG. 16. TWEAK is a negative regulator of skeletal muscle regeneration in mice. TA muscle of wild-type, TWEAK-KO, control and TWEAK-Tg mice were analyzed at different time points after cardiotoxin injury. A). Representative Hematoxylin and Eosin (H&E) staining data presented here suggest that regeneration of skeletal muscle was improved in TWEAK-KO mice and reduced in TWEAK-Tg mice compared to their controls. N=4 at each time point. B). Measurement of fiber cross-sectional area (CSA) in H&E-stained sections 10 days after cardiotoxin injection showed that the size of regenerating myofibers was increased in TWEAK-KO and reduced in TWEAK-Tg mice compared to their controls suggesting that TWEAK is a negative regulator of muscle growth.
Figure 16B:
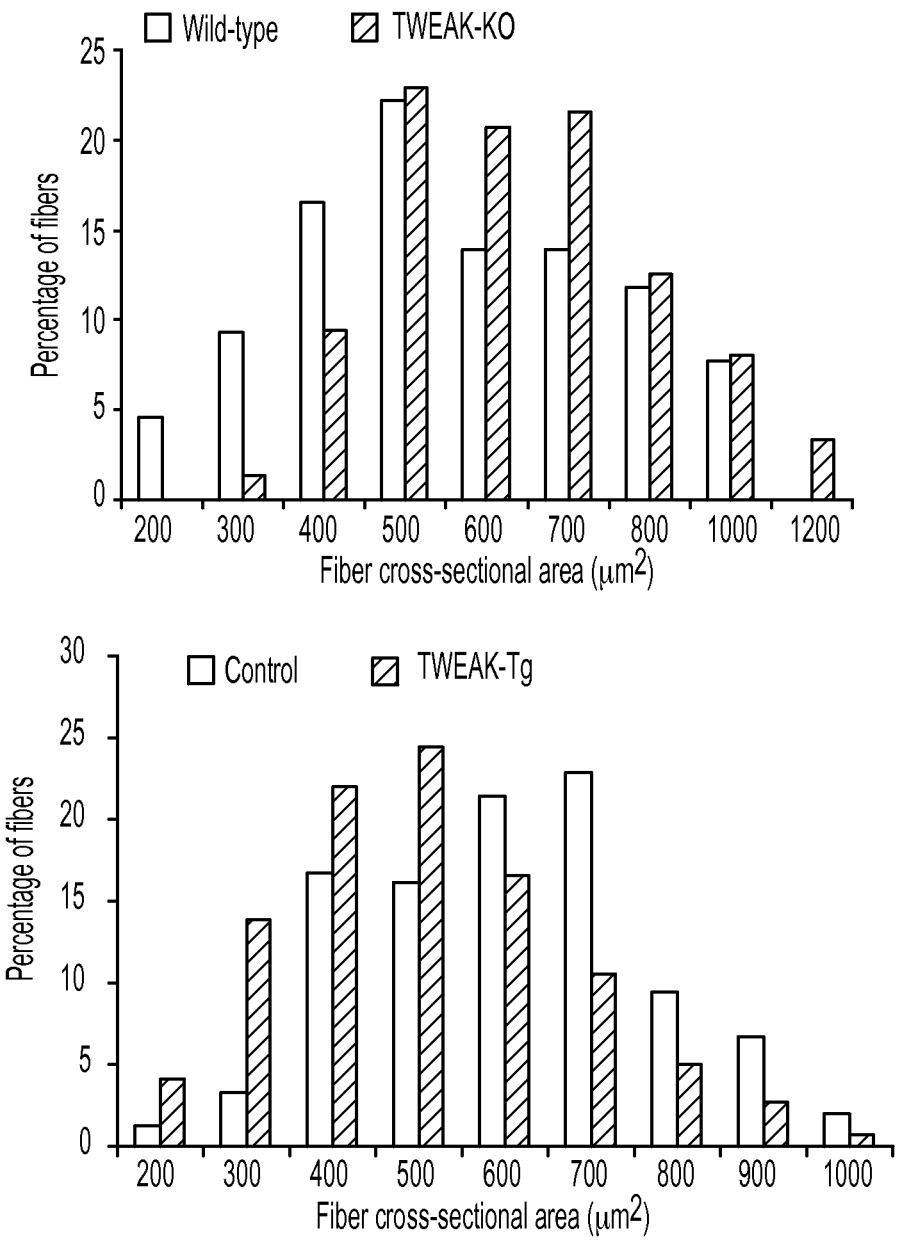
Figure 17:
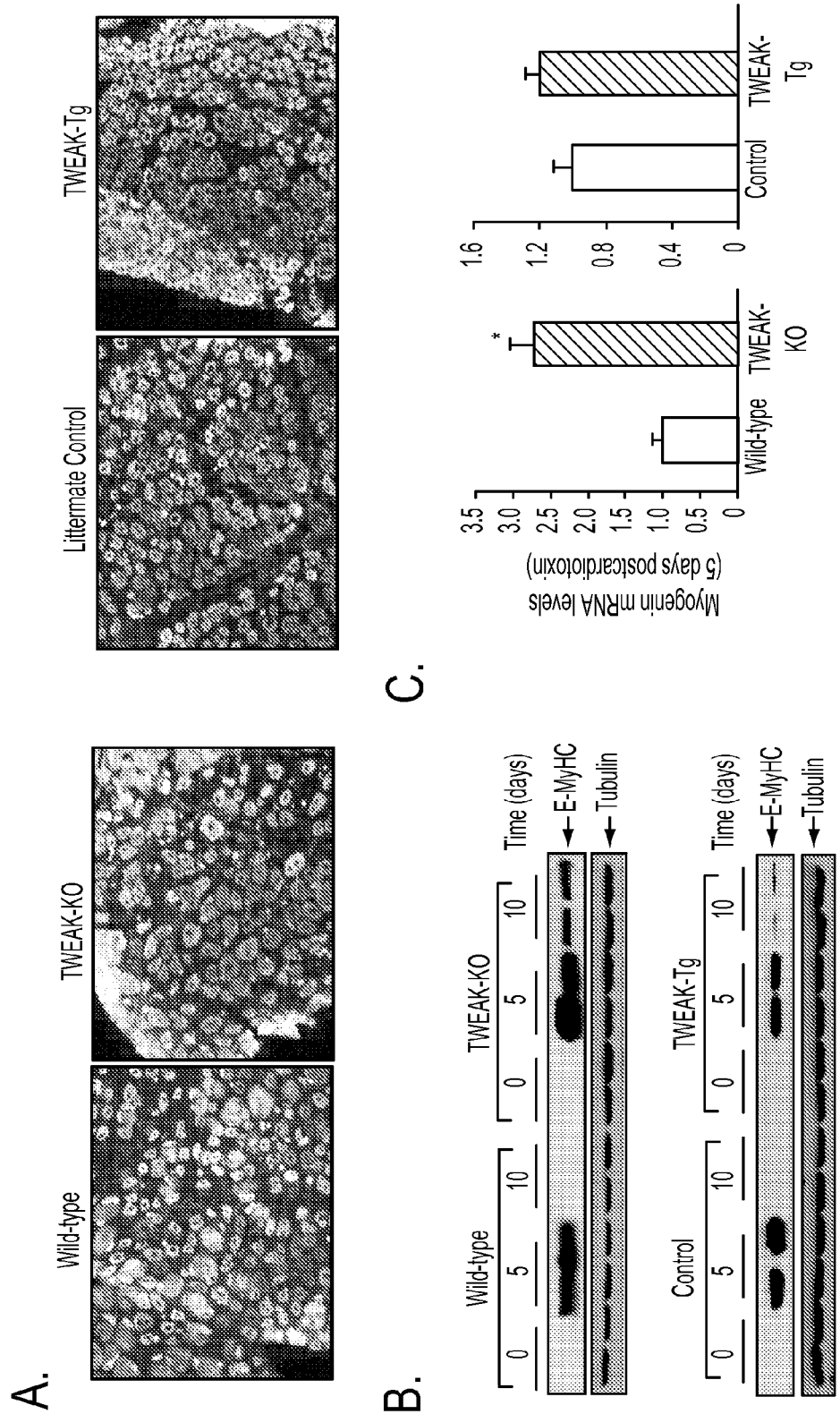
FIG. 17. TWEAK reduces the expression of developmental/embryonic myosin heavy chain (E-MyHC) and myogenin in regenerating TA muscle of mice. A). TA muscle sections from TWEAK-KO and TWEAK-Tg mice and their corresponding controls five days after cardiotoxin injection were stained using E-MyHC antibody. B). Western blot analysis of control, TWEAK-Tg and TWEAK-KO mice showed increased expression of E-MyHC in TWEAK-KO and reduced expression in TWEAK-KO mice compared to control mice 5 and 10 days after cardiotoxin-mediated injury. C). Real-time PCR analysis showed increased mRNA levels of myogenin in TWEAK-KO mice compared to wild-type mice measured 5 days after cardiotoxin injury. *p<0.01, values significantly different from Wild-type mice. N=3 in each group.
Figure 18:
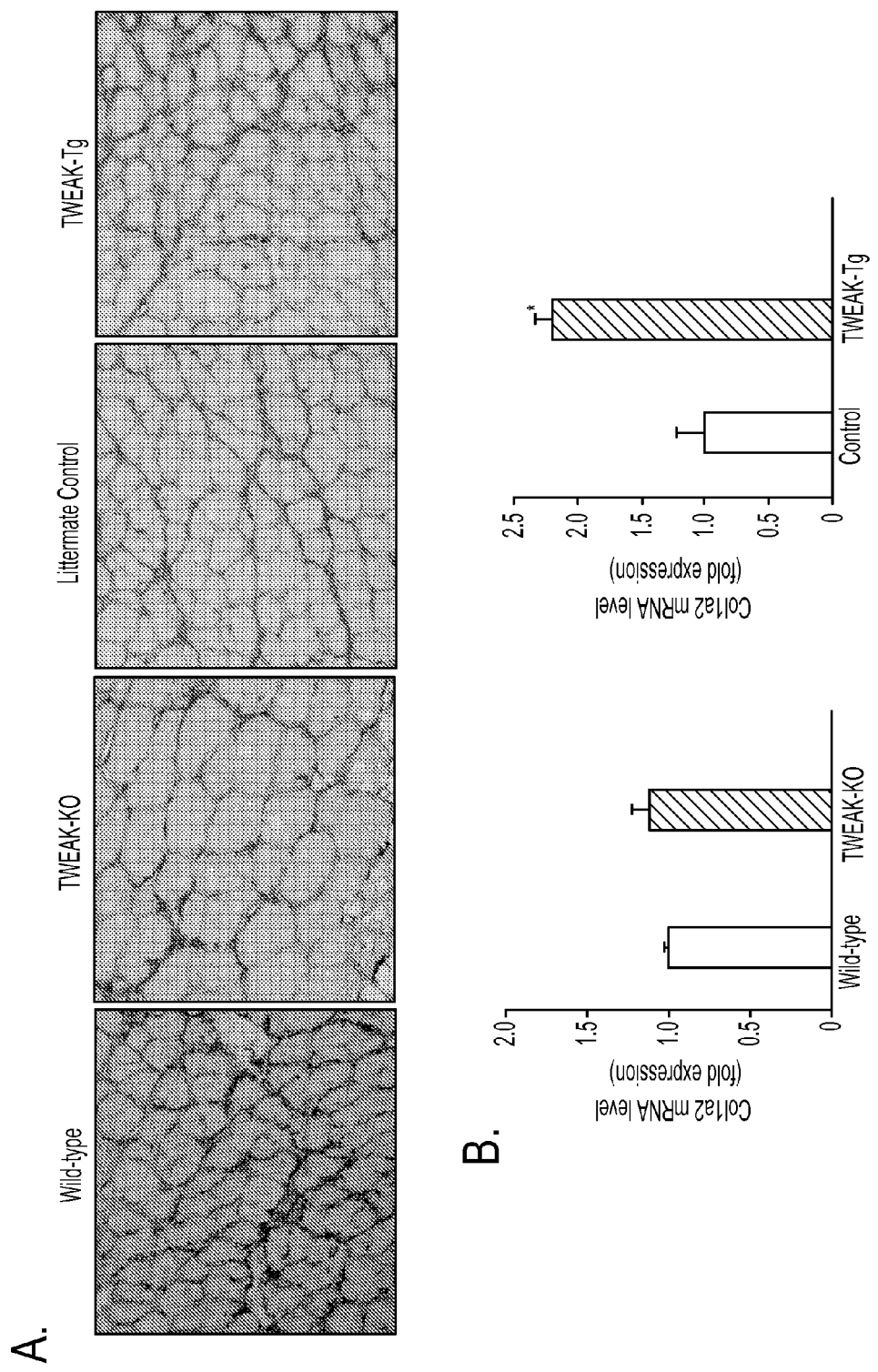
FIG. 18. TWEAK augments the level of fibrosis in regenerating TA muscle of mice. A). TA muscle sections from TWEAK-KO and TWEAK-Tg and their corresponding control mice 10 days after cardiotoxin injection were used to perform Sirius red staining to measure the extent of fibrosis. Representative photomicrographs presented here demonstrate that the level of fibrosis was reduced in TWEAK-KO mice and augmented in TWEAK-Tg mice compared to control mice. B). Transcript level of collagen I (a major collagen in skeletal muscle tissues) was significantly higher in TWEAK-Tg mice compared to control mice measured by QRT-PCR assay. Increased fibrosis may be one of the potential mechanisms by which TWEAK inhibits skeletal muscle regeneration.
Figure 19:
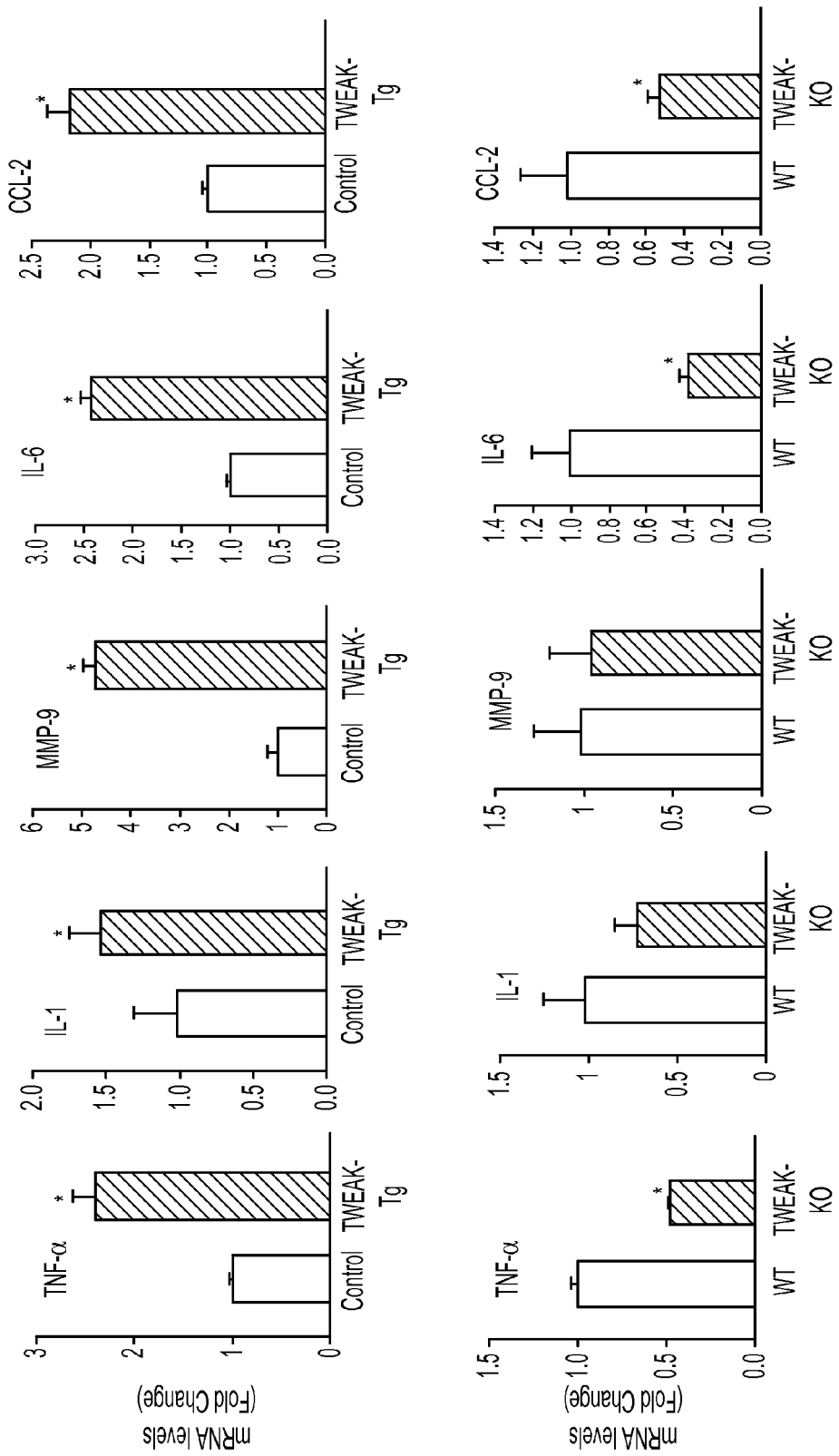
FIG. 19. TWEAK stimulates the expression of proinflammatory molecules in regenerating skeletal muscle. The mRNA levels of various proinflammatory molecules were measured in regenerating skeletal muscle of wild-type and TWEAK-KO mice and control and TWEAK-Tg mice five days after cardiotoxin injury by QRT-PCR. A). Data presented here show that transgenic overexpression of TWEAK augments the mRNA levels of TNF-$\alpha$, IL-1$\beta$, MMP-9, CCL-2, and IL-6 gene in regenerating TA muscle. *p<0.01, values significantly different from TA muscle of control mice. B). The mRNA levels of TNF-$\alpha$, IL-6 and CCL2 were significantly lower in TWEAK-KO mice compared to wild-type (WT) mice. *p<0.01, values significantly different from TA muscle of wild-type mice. N=4 in each group.
Figure 20:
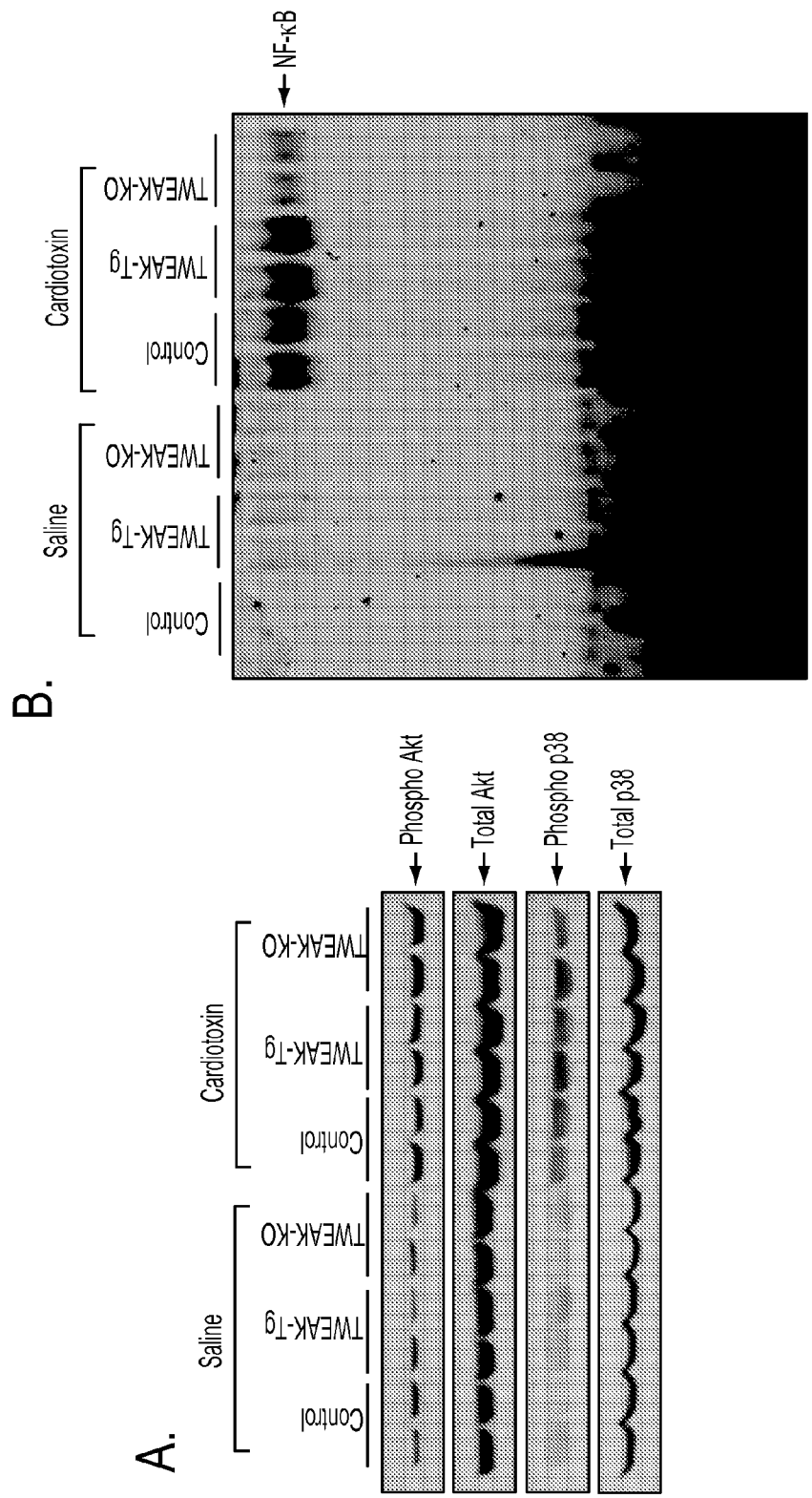
FIG. 20. TWEAK causes the activation of NF-$\kappa$B in regenerating myofibers. A). The western blot analysis showed the activation of p38 or Akt kinase in regenerating skeletal muscle was comparable with corresponding control mice. B). Representative electrophoretic mobility shift assay (EMSA) gel presented here show that the DNA-binding activity of NF-$\kappa$B in regenerating TA muscle was higher in TWEAK-Tg and significantly lower in TWEAK-KO mice.

Inhibition of TWEAK/Fn14 Pathway Improves Skeletal Muscle Regeneration in Response to Injury Similar to denervation model, the studies described herein provide the first evidence that inhibition of the TWEAK/Fn14 pathway is sufficient to improve regeneration of skeletal muscle after injury. This inference is supported by the findings that the a) levels of TWEAK/Fn14 are increased after cardiotoxin-mediated injury in skeletal muscle (FIG. 15); b) genetic deletion of TWEAK improves regeneration and muscle growth after cardiotoxin-mediated injury (FIGS. 16 and 17), and c) overexpression of TWEAK in skeletal muscle (i.e., TWEAK-Tg mice) attenuates muscle regeneration and growth (FIGS. 16 and 17). The mechanisms of action of TWEAK/Fn14 appear to be similar during regeneration or atrophy. Similar to the denervation study, TWEAK was found to increase fibrosis (FIG. 18) in regenerating myofibers in addition to increasing the expression of proinflammatory molecules (FIG. 19). Furthermore, TWEAK augments the activation of NF-κB transcription factor in regenerating skeletal muscle (FIG. 20). Previously published reports have indicated that NF-κB is a negative regulator of skeletal muscle regeneration (Mourkioti et al., *J Clin. Invest.*, 116, 2945-2954 (2006)).

TWEAK/Fn14 is a Target to Counter Disuse-Related Skeletal Muscle Atrophy.

The identification of the TWEAK/Fn14 pathway as a mediator of denervation-induced muscle atrophy indicates that inhibition of this pathway may be beneficial under denervation and disuse conditions, and for the regeneration of skeletal muscle, especially since the deletion of TWEAK was sufficient to maintain muscle strength in addition to mass.

Results

Characterization of TWEAK-Transgenic and TWEAK-Knockout Mice.

To examine the contribution of TWEAK in skeletal muscle physiology and pathophysiology, transgenic mice were generated over-expressing wild-type TWEAK, using the muscle specific creatine kinase promoter (Kronqvist et al., *Am J Pathol.*, 161, 1535-1540 (2002)) (Kronqvist et al., 2002). Previously, founder TWEAK-transgenic mice were produced that expressed high levels (>14 fold) of TWEAK protein. Those mice were significantly smaller in size, and died at perinatal or neonatal stages due to excessive muscle loss (Dogra et al., *FASEB J.*, 21,1857-1869 (2007)). However, by performing additional pronuclear injections of transgenic DNA, two additional TWEAK-Tg lines have been established (FIG. 1A). Certain embodiments of the invention are directed to such mice. Because TWEAK-Tg mice were generated in B6D2F1 background, these mice were crossed with C57BL/6 mice for 7 generations before using for this study. Both of the transgenic lines expressed similar elevated levels of TWEAK in skeletal muscle and showed no major variation in any of the phenotypes reported in this study.

To validate that TWEAK is predominantly expressed in skeletal muscle of TWEAK-Tg mice, mRNA levels of TWEAK were assessed in different tissues of 3 month old TWEAK-Tg and control mice by quantitative real time PCR (QRT-PCR) assay. About 4- to 6-fold increase in level of TWEAK mRNA was consistently observed in skeletal muscle and approximately 1.5-fold in the cardiac muscle of the TWEAK-Tg compared to control mice (FIG. 1A). No significant difference in mRNA levels was observed in liver and spleen (FIG. 1A). To confirm that the increased expression of TWEAK in skeletal muscle of TWEAK-Tg mice leads to elevated levels of TWEAK protein, the protein levels of TWEAK were measured in tissue extracts and serum using Mouse TWEAK/TNFSF12 DuoSet ELISA assay kit (R&D Systems, Minneapolis, Minn.). As shown in FIG. 1B, the levels of TWEAK protein were approximately 3-4 folds higher in skeletal muscle of TWEAK-Tg mice compared to littermate control mice (TWEAK-Tg: 2.88±0.05 ng/mg vs. littermate control: 0.72±0.03 ng/mg protein extracts in TA muscle). No significant difference in the protein levels of TWEAK in other tissues (e.g., heart, liver, and spleen) or serum was observed between TWEAK-Tg and littermate control mice (FIG. 1B). In addition to transgenic mice, TWEAK-knockout (KO) mice were also employed (Maecker et al., *Cell*, 123, 931-934 (2005)) to study the effects of genetic ablation of TWEAK on skeletal muscle. TWEAK-KO mice did not show any overt phenotype. Although body and different organs (e.g., brain, liver, kidney, heart, lung, and thymus) weights were comparable between control and TWEAK-KO mice, a significant increase in number of natural killer has been reported in secondary lymphoid organs of TWEAK-KO mice compared to control mice.

TWEAK functions by binding to the fibroblast growth factor-inducible receptor 14 (Fn14 receptor) in skeletal muscle. Whether overexpression or genetic ablation of TWEAK in 3 months old mice affects the expression of Fn14 in skeletal muscle was examined. Fn14 mRNA levels in skeletal muscle of TWEAK-Tg were comparable to control mice (FIG. 1C). However, mRNA levels of Fn14 were found to be increased by ~1.6 fold in skeletal muscle of TWEAK-KO mice compared to controls (FIG. 1C), suggesting the possibility of a compensatory mechanism that might be activated in the absence of the Fn14 ligand. Transcript levels of TNF-α, IL-1β, and IL-6 in TWEAK-Tg were comparable with controls, indicating the absence of any non-specific inflammation in TWEAK-Tg mice (FIG. 1D). In addition, serum levels of creatine kinase (CK) in TWEAK-Tg and TWEAK-KO mice were also comparable with control mice suggesting that overexpression or genetic ablation of TWEAK does not cause any overt muscle pathology in mice (FIG. 1E).

Transgenic Overexpression of TWEAK Causes Muscle Atrophy In vivo.

Figure 10:
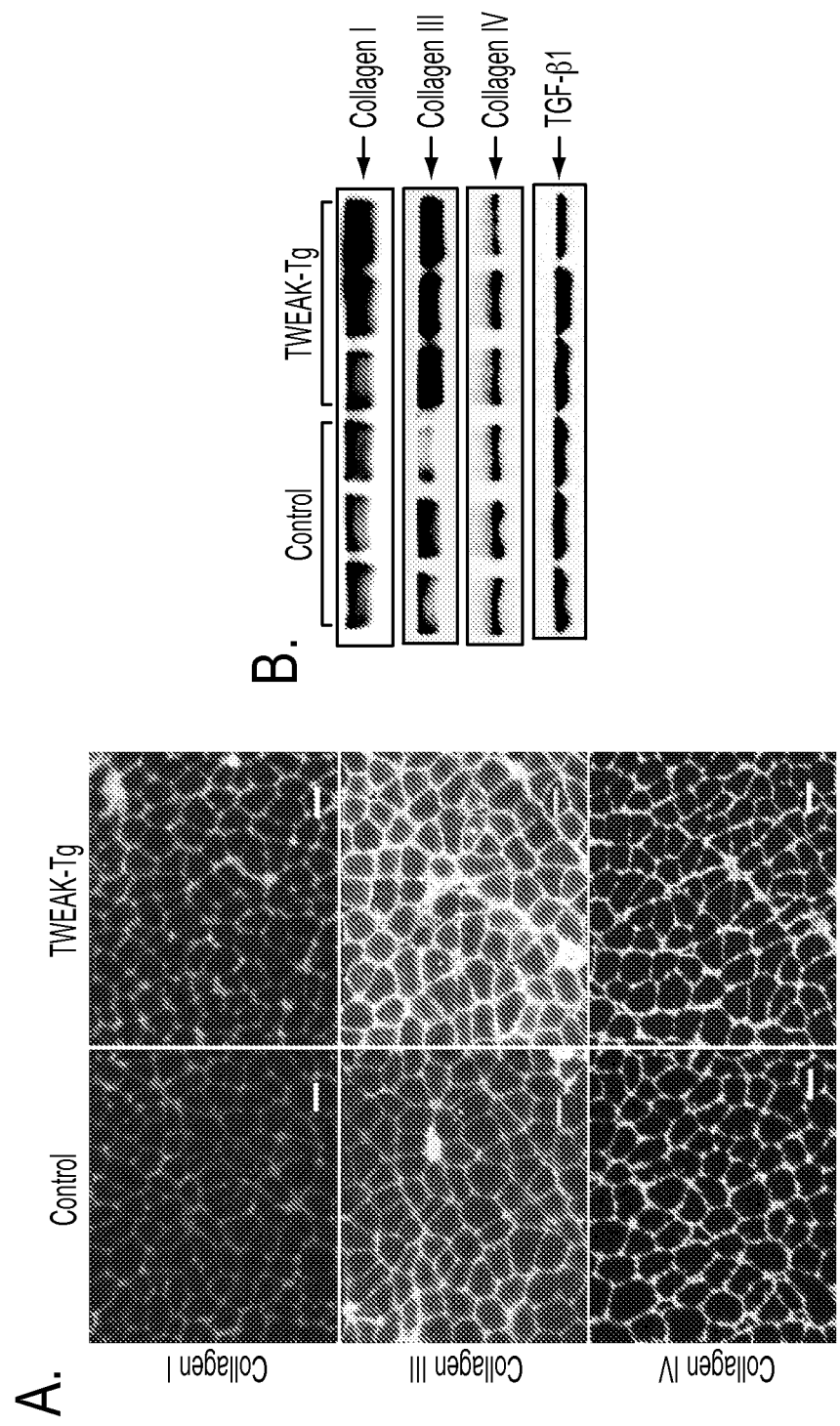
FIG. 10. Expression of collagens in skeletal muscle of control and TWEAK-Tg mice. (A). Immunohistochemical analysis of soleus muscle from 6 months old control and TWEAK-Tg mice using anti-collagen I, anti-collagen III, and anti-collagen IV. Scale bar: 50 μm. (B). Analysis of collagen I, III, and IV and TGF-β in soleus muscle of 6-months old control and TWEAK-Tg mice by western blot.
Figure 11:
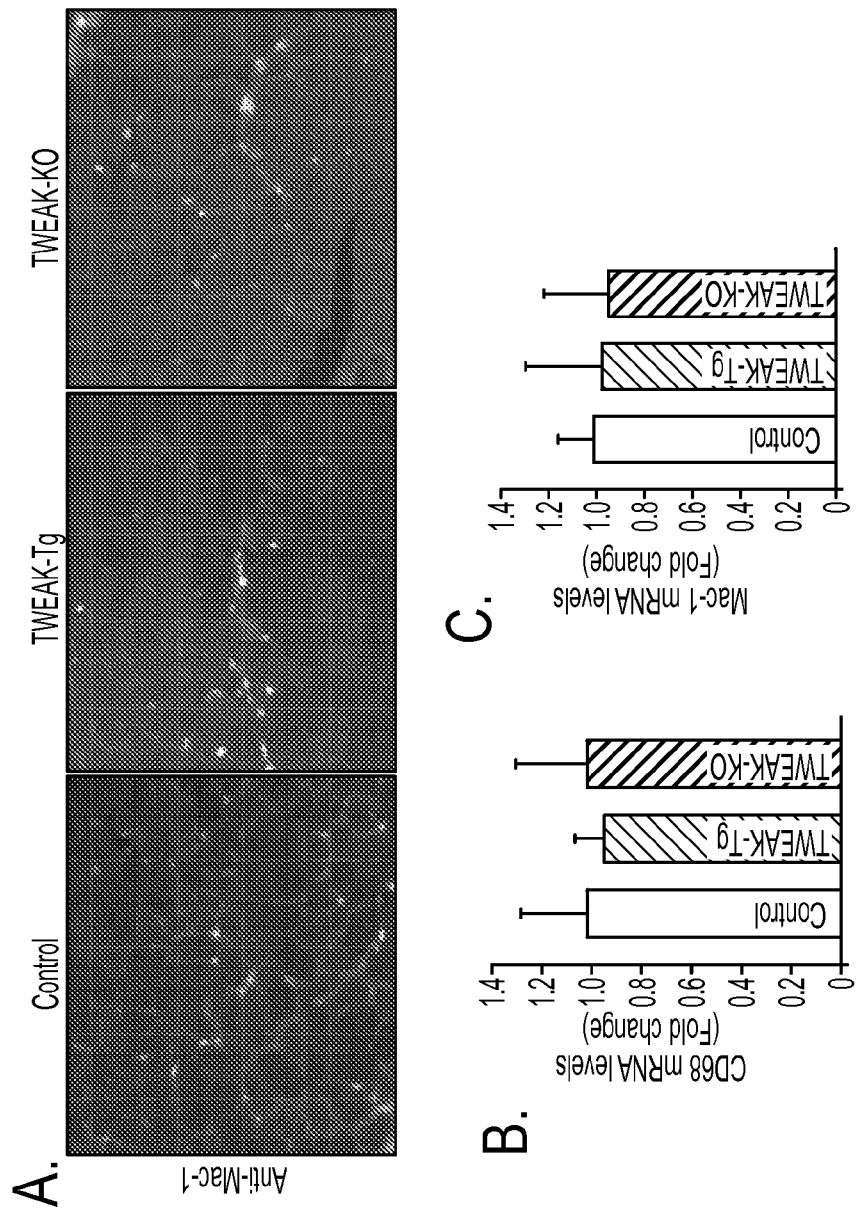
FIG. 11. Quantification of macrophages in skeletal muscle of control, TWEAK-Tg and TWEAK-KO mice. A). Immunohistochemical analysis of soleus muscle from 6 months old control, TWEAK-Tg, and TWEAK-KO mice using Anti-Mac-1. The fold change in mRNA levels of macrophage markers B). CD68, and C). Mac-1 in soleus muscle of TWEAK-Tg and TWEAK-KO mice compared to control mice measured by QRT-PCR assay.

The effects of skeletal muscle specific elevation of TWEAK and the mechanisms by which TWEAK induces muscle loss in vivo have not previously been demonstrated. Hematoxylin and Eosin (H&E) staining did not show any major structural differences in skeletal muscle between control, TWEAK-Tg, and TWEAK-KO mice at 1 or 3 months of age. However, differences in skeletal muscle structure became apparent after 4 months, especially in soleus muscle. The soleus muscle of 6-month old TWEAK-transgenic mice showed reduced fiber size (FIG. 2A). Masson's trichrome staining of muscle sections revealed increased levels of collagen fibers in soleus muscle of 6 months old TWEAK-Tg mice compared to control mice (FIG. 2A, middle panel). Since collagen I, III, and N are the major collagen types in skeletal muscle, how the levels of these collagens change in skeletal muscle of TWEAK-Tg mice compared to control mice was examined. Immunohistochemical analysis revealed increased levels of collagen I and III (but not collagen N) in soleus muscle of 6-month old TWEAK-Tg mice compared to control mice (FIG. 10A). The increased levels of collagen I and III in TWEAK-Tg mice were also confirmed by performing Western blot (FIG. 10B). Since transforming growth factor-β (TGF-β) is a predominant mediator for the development of interstitial fibrosis in different tissues and elevated levels of TGF-β have been observed in various muscular disorders, whether TWEAK affects the expression of TGF-β in skeletal muscle of mice was examined. No significant difference in the level of TGF-β protein between control and TWEAK-Tg was found (FIG. 10B). To evaluate whether increased fibrosis in soleus muscle of TWEAK-Tg mice was due to increased accumulation/infiltration of inflammatory immune cells especially macrophages, the levels of macrophages were studied by performing immunostaining using Mac-1 antibody. However, there was no significant difference in number of macrophages in soleus muscle of control, TWEAK-Tg, and TWEAK-KO mice which was further confirmed by measuring the mRNA levels of CD68 and Mac-1, the major cell surface markers for macrophages by QRT-PCR (FIG. 11). In contrast to TWEAK-Tg mice, TWEAK-KO mice showed normal soleus muscle structure with no indication of inflammation or fibrosis (FIG. 2A, upper and middle panels). The changes in fiber size were quantified after immunostaining soleus muscle sections (FIG. 2A, bottom panels) for laminin and measuring fiber cross-sectional area. The mean fiber cross-sectional area of soleus muscle was reduced by ~33% in 6 months old TWEAK-Tg mice. Further, the average fiber cross-sectional area in soleus muscle of TWEAK-KO mice was about 12% higher compared to age-matched control mice, demonstrating that TWEAK modulates normal muscle size (FIG. 2B).

One of the unique features of skeletal muscle is its composition of different muscle fibers types and its ability to switch fiber type to meet particular physiological demands. To evaluate the role of TWEAK in skeletal muscle fiber type remodeling, double immunostaining was performed on soleus muscle sections using antibody against laminin and an antibody (NovoCasta, Cat #NCL-MHCf) which recognizes all three fast-type fibers IIa, IIx and IIb (Hunter et al., *J Clin Invest.*, 114, 1504-1511 (2004)). Compared to controls (48.3±1.3%), the number of fast-type fibers was increased in TWEAK-Tg (63.6±3.6%), and reduced in TWEAK-knockout (42.8±1.2%) mice (FIGS. 2C, D) indicating that TWEAK favors a transition from slow to fast-type fibers. To further confirm the role of TWEAK in fiber-type switching, immunostaining was performed on extensor digitorum longus (EDL) muscle sections using an antibody (clone A4.840) which recognizes only type I fibers along with laminin antibody. Again the number of slow type fibers was found to be significantly reduced in TWEAK-Tg and significantly increased in TWEAK-KO mice compared to control mice (FIG. 2E, F). Comparison of cross-sectional area of slow and fast type fibers in soleus muscle of control and TWEAK-Tg mice revealed ~36% reduction in fast-type and only ~7.2% in slow-type fibers suggesting that TWEAK-induced atrophy is predominantly restricted to fast-type fibers (FIG. 2G). Taken together, these results suggest that endogenous levels of TWEAK regulates muscle mass, since its deletion results in hypertrophy, and that overexpression of TWEAK is sufficient to induce muscle atrophy in vivo.

Figure 4:
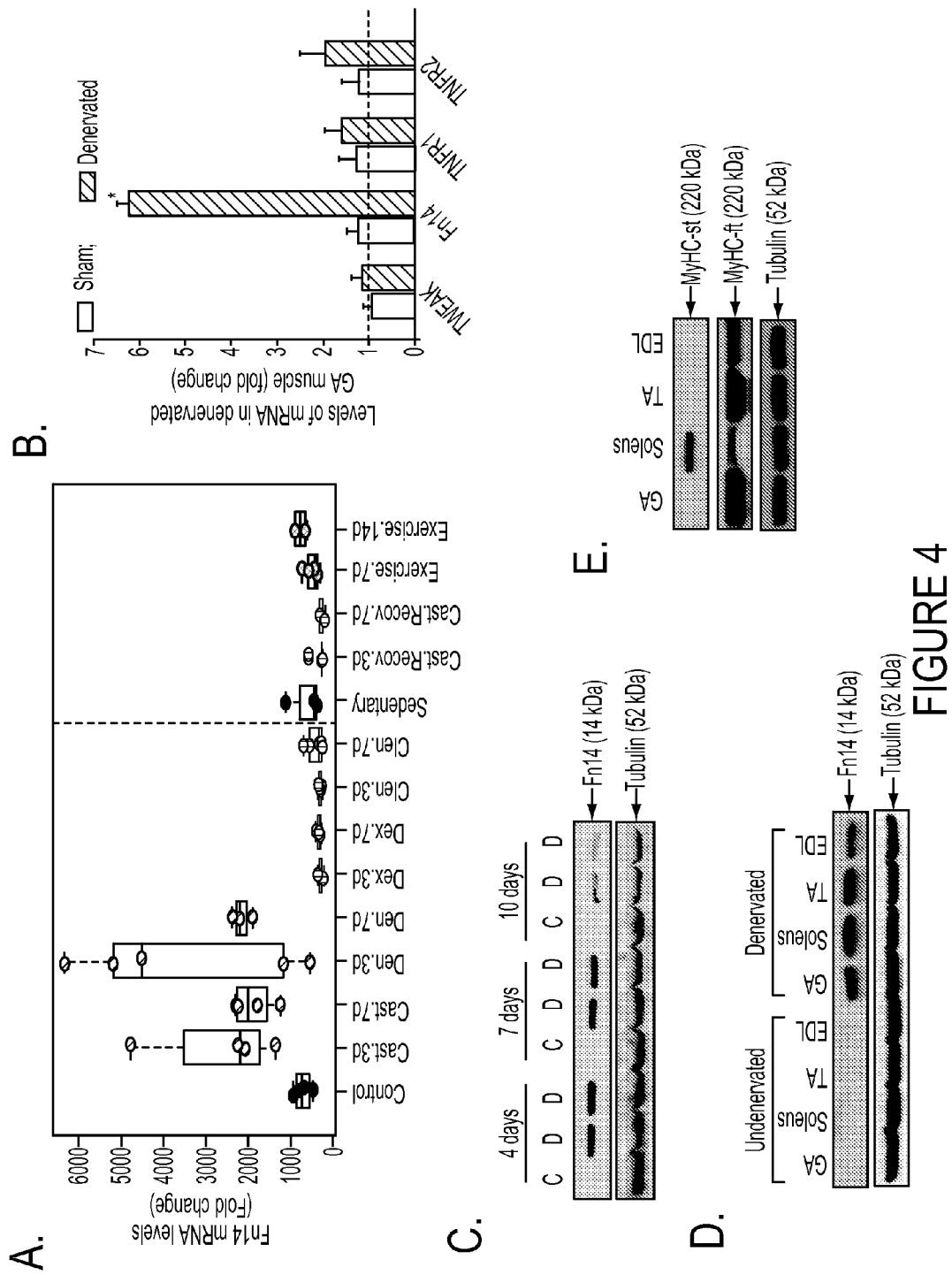
FIG. 4. Expression of TWEAK and Fn14 in skeletal muscle upon denervation. (A) Expression of Fn14 in skeletal muscle in response to casting (Cast.), denervation (Den.), and dexamethasone (Dex.) treatment to induce atrophy, and in response to clenbuterol (Clen.), and recovery (Recov.) from casting to induce hypertrophy. Animals were also studied under free-running exercise conditions (exercise). mRNA was taken at the time points indicated, and assessed in an Affymetrix microarray study. mRNA from ten animals (n=10) were used for each condition. (B) Relative mRNA levels of TWEAK, Fn14, TNFR1 and TNFR2 in denervated gastrocnemius (GA) muscle versus sham-operated contralateral GA muscle after 4 days from 12-week old C57BL/6 mice (n=5, *p<0.01). (C) Levels of Fn14 protein measured by Western blot in control and denervated gastrocnemius muscle of C57BL/6 mice at 4, 7, or 10 days of denervation. (D). Expression of Fn14 protein GA, tibial anterior (TA), soleus, and extensor digitorum longus (EDL) muscle of mice measured four days after denervation. (E). Representative immunoblots showing expression of slow (clone, A4.840) and fast-type MyHC (clone BF-F3) in GA, TA, soleus and EDL muscle of mice. U, undenervated; D, denervated.

Soleus muscle may contain type I and type IIa fibers (*J. Physiol.*, 325, 393-401 (1982)). As described herein, a distinction has been made between type I (slow) and type II (fast). An antibody (NovoCasta, Cat #-NCL-MHCf) has been used that recognizes all type II fibers (e.g., IIa, IIx and IIb fast myosin heavy chain; see FIGS. 2D and E). Soleus muscle in rat and other higher rodents predominantly (>80%) contain slow type fibers. However, the soleus muscle of mice contains only about 50% slow type I fibers (as labeled for slow (type I) and fast (IIa, IIx, IIb)). Indeed, the mouse soleus is an excellent example of a mixed muscle in the mouse. The vast majority of muscles in mouse are fast, with varying amounts of IIa, IIx, and IIb. Two different antibodies were used that label fast-type fibers including the antibody (NCL-MHCf) which was used for immunohistochemistry. Almost all the fibers in TA, gastrocnemius, and EDL stained positive for fast-type antibodies. This was also confirmed by performing western blotting for both fast (using BF-F3 antibody, Developments studies hybridoma bank (DSHB), University of Iowa) and slow-type fibers (A4.840, from DSHB). As shown in FIG. 4E, TA, EDL, or gastrocnemius muscle expressed only fast-type myosin heavy chain whereas soleus muscle expressed both fast and slow-type in Western blot. To confirm the discovery that TWEAK promotes slow to fast-type fiber switching, the EDL muscle was stained with antibody that recognizes Type I fiber (clone A4.840). Approximately 5% of the fibers were positively stained with this antibody. Furthermore, the proportion of slow-type fiber was reduced in EDL muscle of TWEAK-Tg mice and increased in TWEAK-KO mice (FIGS. 2E and F).

Western blots have been performed to measure the expression of Fn14 in different hind limb muscles. The Fn14 expression is increased in both slow/mixed (soleus) and fast-type (TA, EDL, or gastrocnemius) fibers. Similar data was also obtained by double immunostaining for Fn14 and slow or fast-type fibers. Based on these results, it can be postulated that Fn14 is expressed in both slow and fast-type fibers upon denervation. However, the binding of TWEAK to Fn14 in slow-type fibers may cause the transition to fast-type followed by atrophy.

TWEAK Triggers Activation of Proteolytic Pathways In vivo.

The mechanism of action by which TWEAK induces skeletal muscle atrophy in vivo was examined. It was of interest to know whether TWEAK induces atrophy by perturbing protein synthesis or proteolysis, and if the latter was activated, whether particular proteins were subjected to degradation in a TWEAK-dependent manner. A marked reduction in the levels of myosin heavy chain (MyHC), tropomyosin, and neuronal nitric oxide synthase (nNOS) was observed in the soleus muscle of TWEAK-Tg mice, whereas TWEAK-KO mice showed an increase in the levels of both MyHC and nNOS proteins, compared to control mice (FIGS. 3A, B, and C). The levels of cytoplasmic proteins troponin and sarcomeric α-actin and cytoskeletal proteins dystrophin and laminin showed no noticeable changes (FIGS. 3A, B).

QRT-PCR analysis revealed no significant changes in mRNA levels of MyHC or nNOS in soleus muscle of TWEAK-Tg and TWEAK-KO mice compared to control mice (FIG. 3D) suggesting that the reduction in the levels of proteins in the TWEAK-transgenic mice was not due to reduced transcription, but rather was a result of a perturbation in protein levels. An increase in proteolysis was suggested downstream of TWEAK activation by the observation that the activation of NF-κB (but not activator protein, AP-1) and level of MuRF1, a muscle-specific E3 ligase which is required for muscle atrophy were significantly higher (1.6±0.2 fold, *p<0.05) in soleus muscle of 6-month old TWEAK-Tg mice compared to control mice (FIGS. 3E, F). It was recently shown that MuRF1 is the NF-κB-regulated E3 ligase for MyHC. Thus, the coincident demonstration of a TWEAK-induced increase in NF-κB and MuRF1, and a decrease in MyHC, suggests that TWEAK promotes atrophy by inducing the degradation of specific muscle proteins in vivo.

Expression of TWEAK Receptor Fn14 is Increased in Denervated Skeletal Muscle.

As described herein, an increase in the level of TWEAK was sufficient to induce muscle atrophy. As described below, it was also determine if the TWEAK/Fn14 pathway perturbed physiologic atrophy. To address this issue, first it was investigated whether the expression of TWEAK, or its receptor Fn14, is affected in skeletal muscle during conditions of atrophy and hypertrophy, in vivo, as determined by Affymetrix microarray analysis. To induce atrophy, twelve-week old mice were treated with a cast on a lower limb for three to seven days, or denervated for three to seven days (meaning the sciatic nerve was transected). To study hypertrophy, the casted muscles were allowed to recover for a week after the casts were removed. Also, as an additional model of hypertrophy, animals were treated with clenbuterol for a week, as described (Hinkle et al., *Muscle Nerve*, 25, 729-734 (2002)). Although TWEAK expression did not change significantly in either settings of atrophy or hypertrophy, the expression of TWEAK receptor Fn14 was upregulated upon casting or denervation (FIG. 4A). Fn14 is not universally upregulated in atrophy conditions, since the glucocorticoid dexamethasone (DEX) did not cause its upregulation (FIG. 4A). In contrast, the expression of Fn14 was found to be somewhat reduced in conditions of hypertrophy, such as clenbuterol and casting recovery (FIG. 4A).

The expression of Fn14 in denervated skeletal muscle was also measured using real-time PCR and Western blot methods. The left sciatic nerve was transected, whereas the right leg was only sham-operated, leaving the right leg as a control. It was once again observed that the mRNA level of Fn14, but not TWEAK, was increased about 6- to 7-fold in denervated gastrocnemius muscle compared to contralateral sham-operated control muscle (FIG. 4B). To determine whether denervation-induced elevation in mRNA level was specific to the TWEAK receptor Fn14, in the same experiment the levels of TNF receptors (TNFR) 1 and 2 (FIG. 4B), which belong to the same TNF receptor super family, of which Fn14 is also a member, were measured. No significant increase in mRNA levels of TNFR1 or TNFR2 was observed between denervated and sham-operated control gastrocnemius muscle (FIG. 4B). Similar to mRNA, the protein level of Fn14 in gastrocnemius muscle was also drastically increased, and the level remained elevated even after 10 days of denervation, indicating a role of TWEAK/Fn14 pathway in skeletal muscle atrophy (FIG. 4C). Whether the increased expression of Fn14 was specific to fiber type (slow or fast) was also investigated. The expression of Fn14 was equally increased in soleus (slow/mixed) and gastrocnemius, TA, and EDL muscles (fast type) upon denervation (FIG. 4D). By performing Western blot, it was confirmed that soleus muscle express both fast and slow-type MyHC whereas gastrocnemius, TA, and EDL muscles express predominantly fast-type fibers (FIG. 4E).

Denervation-Induced Skeletal Muscle Atrophy is Rescued in TWEAK-Knockout Mice

Because the expression of Fn14 in skeletal muscle was considerably increased after denervation, whether the loss of skeletal muscle mass in response to denervation is modulated in TWEAK-Tg or TWEAK-KO mice was determined. Since at 3 months TWEAK-Tg and TWEAK-KO mice did not show any apparent skeletal muscle phenotype, and mice at this age are fully developed, 3 month old mice were used to evaluate the role of TWEAK in denervation-induced loss of skeletal muscle mass. Gross analysis showed that the loss of gastrocnemius muscle was increased in TWEAK-Tg mice and rescued in TWEAK-KO mice compared to control mice 10 days after denervation (FIG. 5A). Indeed, the measurement of individual muscle weight (from tendon to tendon) confirmed that transgenic over-expression of TWEAK stimulates denervation-induced loss of skeletal muscle mass (FIG. 5B). Conversely, TWEAK-KO mice showed reduced loss of skeletal muscle mass upon denervation (FIG. 5B). The fiber cross-sectional area after staining of muscle sections with Hematoxylin and Eosin (H&E) dyes (FIG. 5C) was assessed. The average fiber cross-sectional area in TA muscle was significantly reduced in TWEAK-Tg mice compared to control mice both 10 and 21 days after denervation (FIG. 5D). In contrast, the fiber cross-sectional area was significantly preserved in skeletal muscle of TWEAK-KO mice after denervation (FIG. 5D). Similar results were obtained with soleus (FIGS. 5D and E) and gastrocnemius and EDL muscles.

Fibrosis is an important pathological feature in various muscular disorders, and is observed in paraplegic patients, who suffer from permanent denervation. Since TWEAK-Tg mice showed increased fibrosis at the age of six months (FIG. 2A, middle panel), whether overexpression or genetic ablation of TWEAK in mice affects the extent of fibrosis in skeletal muscle in response to denervation was investigated. Staining of muscle sections with Sirius red dye, which labels collagen fibers, showed a drastic increase in the accumulation of collagen fibers in denervated TA muscle of TWEAK-Tg mice compared to controls. Furthermore, the level of fibrosis was somewhat reduced in denervated TA muscle of TWEAK-KO mice after 21 days of denervation (FIG. 6A). Increased fibrosis in TWEAK-Tg and its reduction in TWEAK-KO mice compared to control mice upon denervation was also confirmed by measuring the mRNA levels of collagen I (i.e., Col1a2, a major collagen in skeletal muscle) in TA and soleus muscles by QRT-PCR technique (FIG. 6B).

Since ablation of TWEAK attenuated muscle atrophy upon denervation, whether the absence of TWEAK also affects muscle force production in isometric contraction in denervated skeletal muscle was determined. A significant decrease in soleus muscle absolute force production after denervation in control mice was noted, which was significantly preserved in TWEAK-KO mice (FIG. 6C). These results further support the discovery that blocking TWEAK represents a promising strategy to counteracting skeletal muscle atrophy elicited, e.g., by denervation.

Pharmacological Inhibition of TWEAK Attenuates Denervation-Induced Skeletal Muscle Atrophy in Mice.

Since the loss of skeletal muscle mass in response to denervation was significantly reduced in TWEAK-KO mice, whether blockage of TWEAK activity using a rat anti-mouse TWEAK neutralizing antibody (clone MTW-1) prevents the denervation-induced skeletal muscle loss in mice was investigated. C57BL6 mice were denervated for two days followed by intraperitoneal injections of either MTW1 antibody (200 μg/mouse) or isotype control (200 μg/ml) every third day (total three injections). Interestingly, treatment of mice with MTW1 antibody significantly increased the fiber cross-sectional area in denervated TA and soleus muscle of MTW1-treated mice compared to isotype control-treated mice (FIG. 7). These results further confirm that TWEAK is an important mediator of denervation-induced skeletal muscle atrophy.

TWEAK is an Upstream Activator of NF-κB in Denervated Skeletal Muscle.

NF-κB is a transcription factor which causes skeletal muscle-wasting, and which is activated by cytokines. To understand the intracellular signaling mechanisms by which TWEAK-Fn14 stimulates the loss of skeletal muscle mass in response to denervation, the activation of NF-κB in control and denervated skeletal muscle of TWEAK-Tg and TWEAK-KO mice was measured. DNA-binding activity of NF-κB, measured by electrophoretic mobility shift assay (EMSA), was found to be significantly increased in denervated muscle of TWEAK-Tg mice as compared to control mice (FIG. 8A). On the other hand, the denervation-induced activation of NF-κB was significantly reduced in TWEAK-KO mice (FIG. 8B). To confirm that the retarded bands seen in EMSA are indeed NF-κB and to investigate which subunits of NF-κB are activated in denervated skeletal muscle, a supershift assay was performed. Pre-incubation of nuclear extracts from denervated gastrocnemius muscle of control mice with antibodies against p50 or p52 shifted the bands to higher levels of molecular weight, indicating that NF-κB/DNA complex analyzed by EMSA constitutes these proteins (FIG. 8C). Furthermore, by electroporating TA muscle with NF-κB reporter plasmid, it was also confirmed that the observed changes in the DNA-binding activity of NF-κB in denervated skeletal muscle of control, TWEAK-Tg, and TWEAK-KO mice are highly correlated with the transcriptional activation of NF-κB (FIG. 8D).

Besides NF-κB, the PI3K/Akt signaling pathway is also an important regulator of skeletal muscle mass in vivo. Activation of Akt augments skeletal muscle mass in vivo by stimulating anabolic and suppressing catabolic pathways. It has been reported that denervation causes suppression of Akt activity in skeletal muscle whereas constitutive activation of Akt blunts the loss of skeletal muscle mass upon denervation. Whether the phosphorylation of Akt and its downstream targets such as GSK3β, p70S6K, and mTOR were affected in skeletal muscle of TWEAK-Tg and TWEAK-KO mice after denervation was examined. Although levels of phosphorylated Akt, mTOR, p70S6K, and GSK3β were reduced in gastrocnemius muscle 10 days after denervation, there was no noticeable difference in the levels of phosphorylated Akt, mTOR, GSK3β, or p70S6K between denervated muscle of control, TWEAK-Tg, and TWEAK-KO mice (FIG. 12).

TWEAK Acts through Upregulation of Ubiquitin-Proteasome System.

Figure 9:
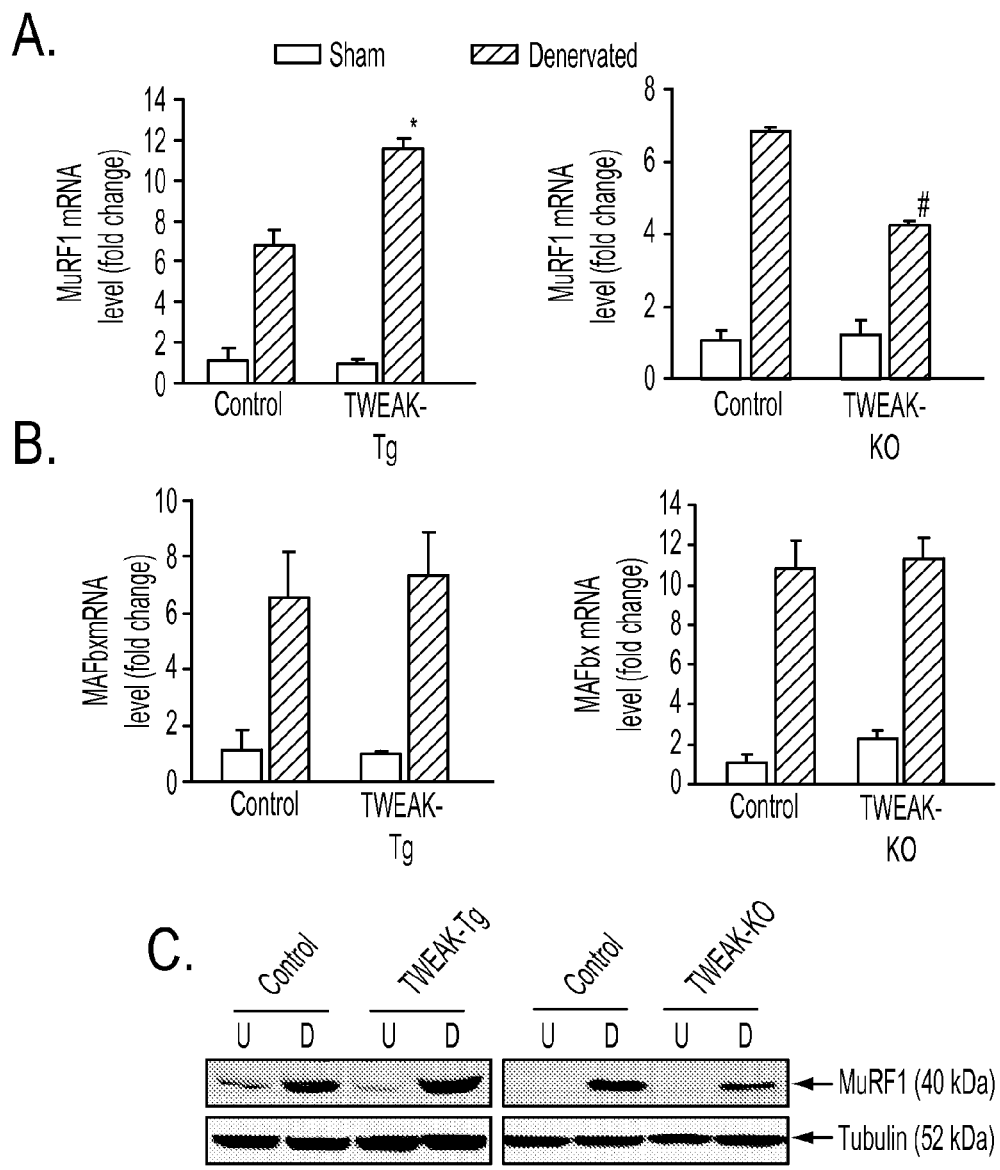
FIG. 9. Effects of TWEAK on the expression of muscle-specific E3 ubiquitin ligases in denervated skeletal muscle. (A) Relative mRNA of MAFbx in denervated gastrocnemius muscle of TWEAK-Tg or TWEAK-KO versus control mice (n=6 in each group). (B) Relative mRNA of MuRF1 in denervated gastrocnemius muscle of TWEAK-Tg or TWEAK-KO versus control mice (n=6 per group). */# $p<0.01$, values significantly different from corresponding control mice. (C) Representative immunoblots demonstrating MuRF1 protein levels in undenervated and denervated gastrocnemius muscle of control, TWEAK-Tg and TWEAK-KO mice. U, undenervated; D, denervated.

To investigate the mechanisms by which TWEAK induces atrophy in denervated skeletal muscle, whether the activity of the ubiquitin-proteasome system, which plays a prominent role in catabolic loss of skeletal muscle mass, was affected in TWEAK-Tg or TWEAK-KO mice was investigated. The expression patterns of MAFbx and MuRF1 by QRT-PCR in the Tg and KO animals, vs. controls were studied. The expressions of both MAFbx and MuRF1 were significantly increased in denervated gastrocnemius muscle compared to sham-operated control muscle (FIGS. 9A and B). The mRNA levels of MuRF-1 was significantly increased in TWEAK-Tg and significantly decreased in TWEAK-KO mice (FIG. 9B), consistent with MuRF1 being regulated by NF-κB activation. In contrast, there was no significant difference in the level of MAFbx expression between denervated muscle of control, TWEAK-Tg, and TWEAK-KO mice (FIG. 9A), which is again consistent with a prior report showing activation of NF-κB induced MuRF1 but not MAFbx expression. Furthermore, by performing Western blot, it was found that the protein level of MuRF1 was also elevated in TWEAK-Tg and reduced in TWEAK-KO mice compared to control mice in denervated muscles (FIG. 9C).

It should be noted that in the nave, undenervated, transgenic animals, NF-κB (FIG. 8A) or MuRF1 (FIG. 9B) was not upregulated. This is because these experiments were done on three month old animals, before a phenotype is seen in the transgenics. By 6 months of age, atrophy, fibrosis, and NF-κB and MuRF1 upregulation is noted in unperturbed animals (FIGS. 2 and 3).

Figure 13:
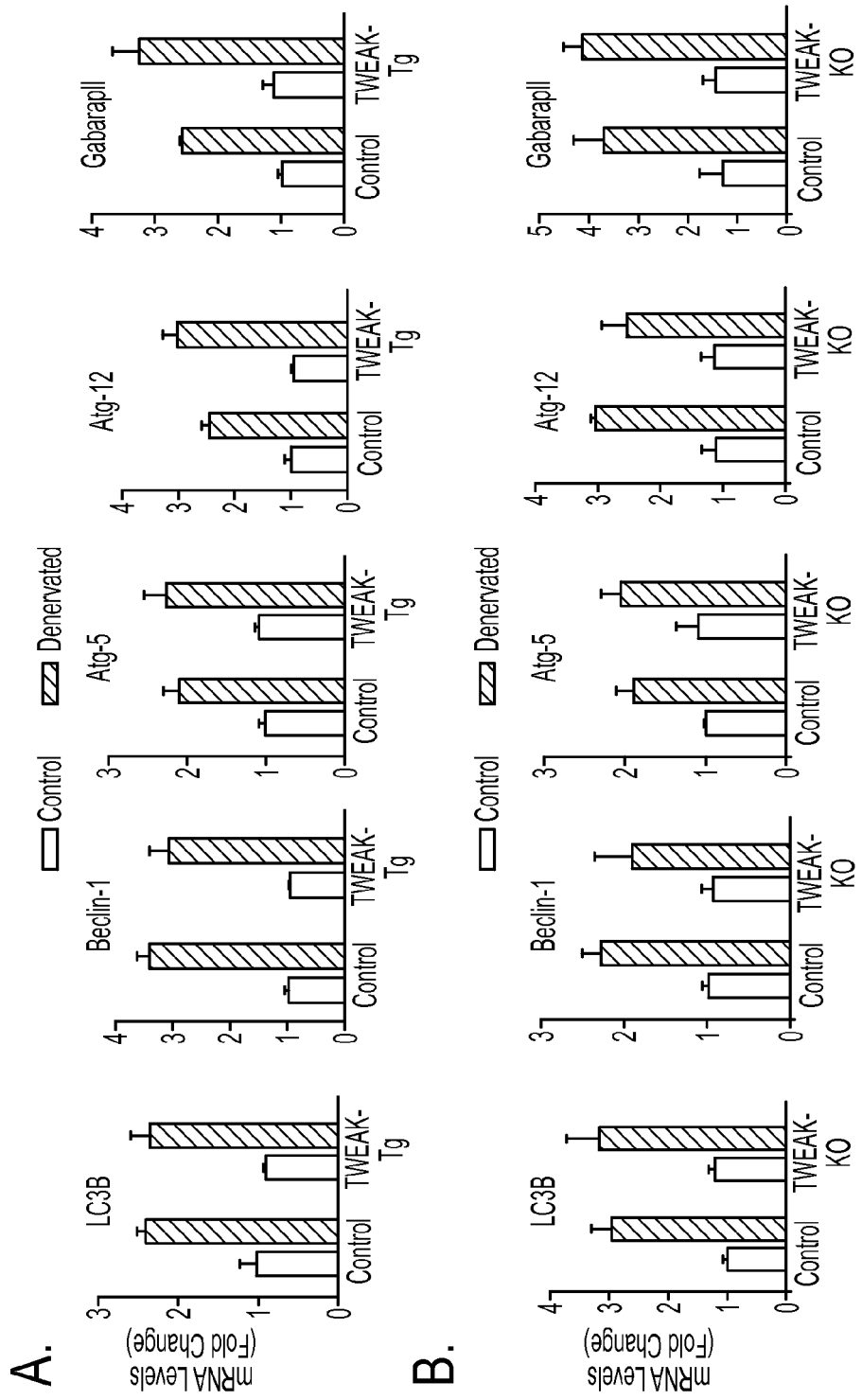
FIG. 13. Expression of autophagy-related genes in denervated skeletal muscle. The fold change in mRNA levels of LC3B, Beclin1, Atg-5, Atg-12, and Gabarapl1 genes was measured in control and denervated gastrocnemius muscle of (A) TWEAK-Tg and (B) TWEAK-KO using QRT-PCR method. Data presented here demonstrate that there was no significant difference in mRNA levels of LC3B, Beclin1, Atg-5, Atg-12, or Gabarapl1 in denervated GA muscle of TWEAK-Tg or TWEAK-KO compared to control mice. N=6 in each group.

To understand whether TWEAK affects autophagy, mRNA levels of autophagy-related molecules LC3B, Beclin-1, Atg-5, Atg-12, and Gabarapl1 was compared in denervated muscle of control, TWEAK-Tg and TWEAK-KO mice. Although a significant increase in mRNA levels of all the five genes was observed in denervated skeletal muscle, there was no significant difference in the mRNA levels of any of these genes in denervated muscle of TWEAK-Tg or TWEAK-KO mice compared to control mice (FIG. 13).

TWEAK and Fn14 Expression is Increased in Skeletal Muscle in Response to Unloading.

Figure 14:
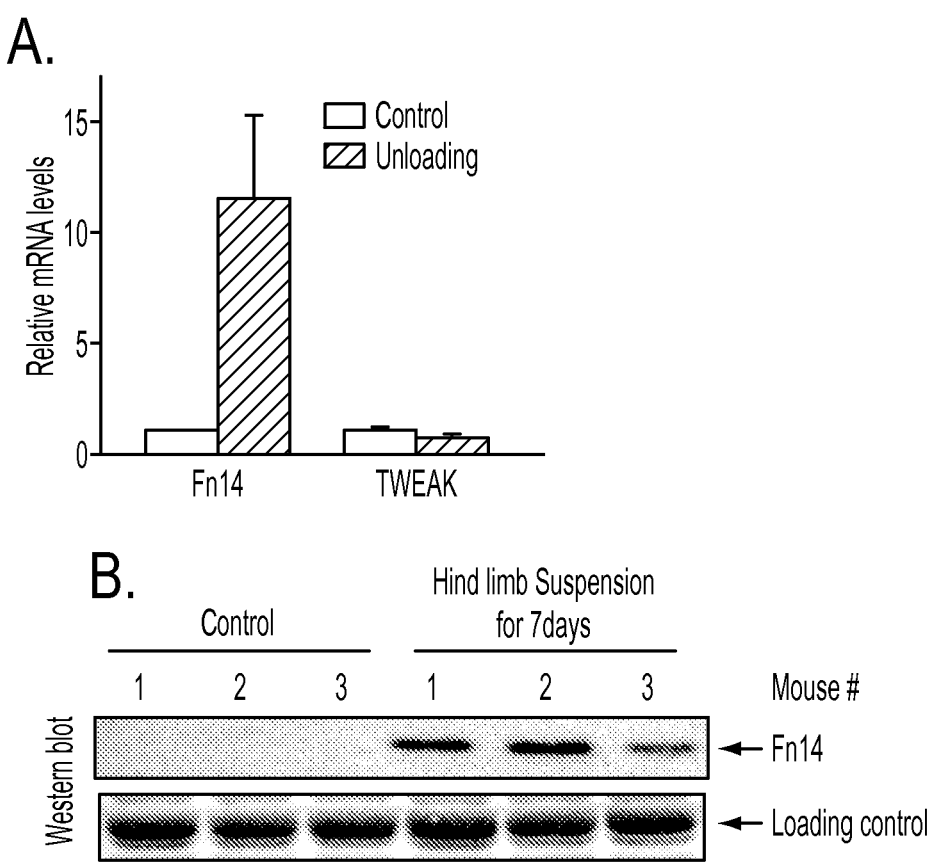
FIG. 14. Expression of Fn14 is dramatically increased in skeletal muscle in response to hind limb unloading. As depicted in (A) and (B), similar to denervation, the expression of Fn14 is dramatically increased in skeletal muscle in response to hind limb unloading (i.e., suspension), further demonstrating that TWEAK/Fn14 is a therapeutic target to prevent disuse-related muscle atrophy.

The role of TWEAK and Fn14 in other models of disuse atrophy was also investigated. Normal C57BL6 mice were subjected to hind limb unloading using a standard protocol. After 7 days, the mice were sacrificed, the hind limb muscles were isolated, and used for real-time PCR and Western Blotting. Data showed that the expression of both TWEAK and Fn14 is dramatically increased in soleus muscle of mice subjected to hindlimb unloading compared to normal controls (FIG. 14). These results provide additional evidence that TWEAK/Fn14 is an important player in skeletal muscle loss in different disuse conditions.

Expression of TWEAK and its Receptor Fn14 is Significantly Increased in Regenerating Muscle Fibers In vivo.

Cardiotoxin (snake venom) is a widely used agent to induce skeletal muscle injury in animals. Hw the expression of TWEAK and its receptor Fn14 are regulated in skeletal muscle of mice in response to cardiotoxin-mediated injury was investigated. Left side tibial anterior (TA) muscle of wild-type C57BL6 mice were injected with cardiotoxin in phosphate-buffered saline (PBS) whereas contralateral right side muscle were injected with PBS alone. After 5 days, the mice were euthanized and TA muscle isolated was used to study the expression of TWEAK and Fn14 using real-time PCR technique. The expression levels of both TWEAK and Fn14 (FIG. 15) were significantly increased in cardiotoxin injected TA muscle compared to contralateral control mice. These data demonstrate increased expression of TWEAK and Fn14 in skeletal muscle after cardiotoxin injection.

TWEAK Inhibits Skeletal Muscle Regenerating In vivo.

To understand the role of TWEAK/Fn14 system in skeletal muscle regeneration, both TWEAK-transgenic (Tg) and TWEAK-KO mice were used. Transgenic mice expressing 4-6 fold higher levels of TWEAK mRNA in skeletal muscle were generated using muscle creatine kinase promoter. TWEAK-KO mice were also used to study the effects of genetic ablation of TWEAK on regeneration of skeletal muscle. TA muscle of transgenic and knockout and their corresponding control mice were injected with cardiotoxin followed by isolation of TA muscle at 5, 10, and 21 days and performing Hematoxylin and Eosin (H&E) staining. Interestingly, the size of regenerating myofibers was higher in TWEAK-KO mice compared to wild-type mice at all the three time points. In contrast, the myofiber size was found to be reduced in TWEAK-Tg mice compared to littermate control mice (FIG. 16A). These observations were confirmed by quantitative estimation of fiber cross-sectional area (CSA) in regenerating myofibers at 10 days post-cardiotoxin injection (FIG. 16B).

TWEAK Inhibits the Expression of Developmental Form of Myosin Heavy Chain in Regenerating TA Muscle.

To further investigate the role of TWEAK in skeletal muscle regeneration, the levels of developmental/embryonic myosin heavy chain (E-MyHC) were measured in regenerating TA muscle of TWEAK-KO and TWEAK-Tg and their corresponding control mice. Staining of the muscle section with Anti-EMyHC showed that the size of the E-MyHC-positive myofibers was considerably higher in TWEAK-KO mice compared to wild-type mice. In contrast, the size of the E-MyHC-positive myofibers was reduced in TWEAK-Tg compared to control mice (FIG. 17A). Western blotting was performed to quantify the amount of E-MyHC in regenerating TA muscle of TWEAK-KO and TWEAK-Tg mice. Interestingly, the protein level of E-MyHC was found to be considerably higher in TWEAK-KO mice compared to wild-type mice 5 days after cardiotoxin injection (FIG. 17B). Conversely, the levels of E-MyHC were reduced in TWEAK-Tg mice compared to corresponding littermate control mice. At 10 days post-cardiotoxin injection, E-MyHC was undetectable in control mice. However, considerable amount of E-MyHC was still present at 10 days in TWEAK-KO mice. Interestingly, a small amount of E-MyHC was also observed in TWEAK-Tg mice though its level was considerably lower as compared to TWEAK-KO mice at 10 days (FIG. 17B).

How the expression of myogenin (a marker for myogenesis) was affected in regenerating myofibers in TWEAK-Tg and TWEAK-KO mice was investigated. The mRNA levels of myogenin were found to be significantly increased in TWEAK-KO mice compared to wild-type. On the other the levels of myogenin were comparable in control and TWEAK-Tg mice (FIG. 17C).

TWEAK Induces Fibrosis in Regenerating Myofibers.

Since increased fibrosis can inhibit the regeneration of myofibers, the role of TWEAK in development of interstitial fibrosis in regenerating myofibers was investigated. TA muscle sections prepared TWEAK-KO and TWEAK-Tg and corresponding control mice were stained with Sirius red dye to study the level of fibrosis. Interestingly, the level of fibrosis was significantly reduced in TWEAK-KO mice compared to wild-type mice. In contrast, fibrosis was markedly higher in TWEAK-Tg mice 10 days after cardiotoxin injection (FIG. 18A). The levels of Collagen I, a major collagen in skeletal muscle tissues, was also measured. The level of collagen I was again found to be significantly reduced in TWEAK-Tg mice and increased in TWEAK-KO mice compared to corresponding control mice (FIG. 18B). These data suggest that TWEAK is an important mediator of development of fibrosis in regenerating skeletal muscle in vivo.

TWEAK Stimulates the Expression of Inflammatory Molecules in Regenerating Myofibers.

How TWEAK regulates the expression of various inflammatory molecules in regenerating myofibers was investigated. Cardiotoxin-injected TA muscle isolated from control, TWEAK-KO and TWEAK-Tg mice were used to measure the transcript levels of various proinflammatory molecules by QRT-PCR. As shown in FIG. 19A, the mRNA levels of inflammatory cytokines (e.g. TNF-α, IL-1β, and IL-6), chemokine CCL-2, and matrix degrading enzyme MMP-9 were found to be significantly increased TWEAK-Tg mice compared to control mice. Furthermore, the mRNA levels of TNF-α, IL-6, and CCL-2 were significantly reduced in TWEAK-KO mice compared to wild-type mice (FIG. 19B).

Activation of NF-κB Transcription Factor in Regenerating Myofibers is Reduced in TWEAK-KO Mice and Increased in TWEAK-Tg Mice.

To understand the mechanisms of action of TWEAK in skeletal muscle regeneration, how TWEAK affects the activation of various cell signaling pathways in myofibers was investigated. While the activation of Akt kinase and p38 mitogen-activated protein kinase (MAPK) promotes regeneration, the activation of NF-κB inhibits skeletal muscle regeneration. By performing Western blot and using antibodies against phospho-Akt and phospho-p38, the activation of these kinases in normal and cardiotoxin-injected TA muscle of control, TWEAK-Tg and TWEAK-KO mice were measured. The activation of both Akt and p38MAPK was increased in cardiotoxin-injected TA muscle. However, the levels of phosphorylated Akt or p38MAPK were comparable between control, TWEAK-Tg and TWEAK-KO mice (FIG. 20A) suggesting that TWEAK does not affect the activation of these molecules in regenerating myofibers.

The role of TWEAK in NF-κB activation was investigated by performing electrophoretic mobility shift assay. As shown in FIG. 20B, the level of activation of NF-κB in cardiotoxin-injected TA muscle was significantly higher in TWEAK-Tg mice and significantly reduced in TWEAK-KO mice compared to control mice (FIG. 20B). These results indicate that TWEAK inhibits skeletal muscle regeneration by augmenting the activation of NF-κB transcription factor Methods Animal Models. Transgenic mice expressing full length TWEAK cDNA under the control of muscle creatine kinase (MCK) promoter were generated as described (Dogra et al., *FASEB J.*, 21, 1857-1869 (2007)). Generation of TWEAK-knockout mice has been previously described (Maecker et al., *Cell*, 123, 931-934 (2005)). All the mice were in C57BL/6 background and their genotype was determined by PCR from tail DNA.

To induce atrophy, twelve-week old mice were either casted or denervated for three to seven days, as previously described (Bodine et al., *Science*, 294, 1704-1708 (2001)). To study hypertrophy, the casted muscles were allowed to recover for a week after the casts were removed. Also, as an additional model of hypertrophy, animals were treated with clenbuterol for a week, as described (Kline et al., *J Appl Physiol.*, 102, 740-747 (2007)). Sciatic denervation was performed by anesthetizing the mice with an intraperitoneal injection of ketamine (100 mg/kg) and xylazine (20 mg/kg); shaving the right hind quarters; making a 0.5-cm incision approximately 0.5 cm proximal to the knee on the lateral side of the right leg; separating the muscles and lifting out the sciatic nerve with a surgical hook or forceps; removing a 2-3-mm piece of sciatic nerve; and closing the incision with surgical staples.

For casting, mice were anesthetized, and immobilized at the knee and ankle joints, with the ankle in plantarflexion to maximize atrophy in the posterior compartment muscles. The plaster of Paris cast encompassed one hindlimb. For recovery, after two weeks of atrophy, the cast was removed and the animals were allowed to ambulate freely in their cages. For clenbuterol treatment, the mice received either physiological saline at 1 ml/kg per day, or 3 mg/kg per day clenbuterol (Sigma Co., St. Louis, Mo.) dissolved in water via a subcutaneous injection. Nine days after the denervation surgery, mice were anesthetized with isoflurane and euthanized by CO2 asphyxiation. The left and right legs were shaved, the skin on each leg was resected, and the tibialis anterior, soleus, and medial gastrocnemius muscles were isolated, removed, and weighed. All animal procedures were approved by the Institutional Animal Care and Use Committee and conformed to the American Physiological Society's Guiding Principles in the Care and Use of Animals. For microarrays, Affymetrix mouse 430 version 2 microarrays were used to measure gene expression values. Normalization in our analysis was carried out using the GC-RMA normalization method (Irizarry et al., *Bioinformatics,* 2007, 789-794 (2007)).

For skeletal muscle regeneration studies, animals were anesthetized and a single dose of cardiotoxin (100 μl of a 10 μM stock in 0.9% saline solution) was injected intramuscularly into the right tibial anterior (TA) muscle of 8-week old control, TWEAK-transgenic, and TWEAK-knockout mice. As a control, the contralateral TA muscle was injected in the same animal with sterile 0.9% saline. After injection, animals were returned to their cage and allowed food and water ad libitum. The TA muscle was isolated after 5, 10 or 21 days for biochemical and histological analyses.

To study the effects of a TWEAK neutralizing antibody (from BioLegend, San Diego, Calif.) on denervation-induced muscle loss, 8 weeks old C57BL6 mice were used. Two days after denervation, the mice were treated by intraperitoneal injections of either MTW1 antibody (200 μg/mouse) or isotype control (200 μg/ml) every third day (total three injections). After 24-36 h of final injection, the mice were sacrificed and hind limb muscles were isolated for histological studies.

Electroporation of Plasmid DNA in Tibialis Anterior (TA) Muscle. The injection of plasmid DNA into TA muscle of mice and electroporation were done following a protocol as described (Schertzer et al., *Mol Ther.,* 13, 795-803 (2006)). Briefly, pNF-κB-Luc (Clontech) and pRL-TK renilla luciferase (Promega) were prepared using endotoxin-free kit (Qiagen) and suspended in sterile saline solution in 1:10 ratio. Mice were anesthetized and a small portion of TA muscle of both hind limbs was surgically exposed and injected with 30 μl of 0.5 U/μl hyaluronidase (CalBiochem). Two hours later plasmid DNA (50 μg in 25 μl saline) was injected in TA muscle and one minute following plasmid DNA injection, a pair of platinum plate electrodes was placed against the closely shaved skin on either side of the small surgical incision (such that the electrodes did not contact the muscle) and electric pulses were delivered transcutaneously. Three 20-ms square-wave pulses of 1-Hz frequency at 75V/cm were generated using a Grass stimulator (Grass S88; Quincy, Mass., USA) and delivered to the muscle. The polarity was then reversed and further three pulses were delivered to the muscle. Following electroporation, the wound was closed with surgical clips and mice returned to their cages and fed a standard diet. Three days following electroporation, the left hind limb was denervated whereas the right side was only sham operated. Finally, after 10 days of denervation, the mice were sacrificed, TA muscle was isolated and muscle extracts made were used for measurement of luciferase and renilla activity using a Dual-luciferase reporter assay system (Promega).

RNA Isolation and Quantitative Real-Time PCR (QRT-PCR). RNA isolation and QRT-PCR were performed using a method as previously described (Dogra et al., *J Biol Chem.,* 281, 10327-10336 (2006)). In brief, RNA was extracted from homogenized tissues using TRIzol reagent (Invitrogen) and an RNeasy Mini Kit (Qiagen Inc., Valencia, Calif.) according to the manufacturer's protocol. The quantification of mRNA expression was carried out using the SYBR Green dye method on 7300 Sequence Detection system (Applied Biosystems, Foster City, Calif.). Purified RNA (1 μg) was used to synthesize first strand cDNA by reverse transcription system using Ambion's oligo (dT) primer and Qiagen's Omniscript reverse transcriptase kit. The first strand cDNA reaction (0.5 μl) was subjected to real-time PCR amplification using gene-specific primers. The sequence of primers used is described in Table 1.

TABLE 1

Sequence of the primers for QRT-PCR.

| Gene name | Forward primer (5'-3') | Reverse primer (5'-3') |
|---|---|---|
| TWEAK | GCTACGACCGCCAGATTGGG<br>SEQ ID NO: 1 | GCCAGCACACCGTTCACCAG<br>SEQ ID NO: 2 |
| Fn14 | AAGTGCATGGACTGCGCTTCTT<br>SEQ ID NO: 3 | GGAAACTAGAAACCAGCGCCAA<br>SEQ ID NO: 4 |
| MyHCf | CGGCAATGAGTACGTCACCAAA<br>SEQ ID NO: 5 | TCAAAGCCAGCGATGTCCAA<br>SEQ ID NO: 6 |
| nNOS | AACCGAATACAGGCTGACGATG<br>SEQ ID NO: 7 | GGGCACGGATTCATTCCTTT<br>SEQ ID NO: 8 |
| Atrogin-1 | GTCGCAGCCAAGAAGAGAAAGA<br>SEQ ID NO: 9 | TGCTATCAGCTCCAACAGCCTT<br>SEQ ID NO: 10 |
| MuRF1 | TAACTGCATCTCCATGCTGGTG<br>SEQ ID NO: 11 | TGGCGTAGAGGGTGTCAAACTT<br>SEQ ID NO: 12 |
| TNF-α | GCATGATCCGCGACGTGGAA<br>SEQ ID NO: 13 | AGATCCATGCCGTTGGCCAG<br>SEQ ID NO: 14 |
| Mac-1 | AGGGTTGTCCAGCCGATGATAT<br>SEQ ID NO: 15 | CCCAGCTTCTTGACGTTGTTGA<br>SEQ ID NO: 16 |
| CD68 | TTACTCTCCTGCCATCCTTCACGA<br>SEQ ID NO: 17 | CCATTTGTGGTGGGAGAAACTGTG<br>SEQ ID NO: 18 |

TABLE 1-continued

Sequence of the primers for QRT-PCR.

| Gene name | Forward primer (5'-3') | Reverse primer (5'-3') |
|---|---|---|
| IL-1β | CTCCATGAGCTTTGTACAAGG<br>SEQ ID NO: 19 | TGCTGATGTACCAGTTGGGG<br>SEQ ID NO: 20 |
| IL-6 | CCTTCTTGGGACTGATGCTGG<br>SEQ ID NO: 21 | GCCTCCGACTTGTGAAGTGGT<br>SEQ ID NO: 22 |
| TNFR1 | AACCAGTTCCAACGCTACCTGA<br>SEQ ID NO: 23 | AGAAAGAACCCTGCATGGCA<br>SEQ ID NO: 24 |
| TNFR2 | TAAGTGCCATCCCAAGGACACTCT<br>SEQ ID NO: 25 | CCCAGTGATGTCACTCCAACAATC<br>SEQ ID NO: 26 |
| LC3B | CTGGTGAATGGGCACAGCATG<br>SEQ ID NO: 27 | CGTCCGCTGGTAACATCCCTT<br>SEQ ID NO: 28 |
| Beclin-1 | TGAAATCAATGCTGCCTGGG<br>SEQ ID NO: 29 | CCAGAACAGTATAACGGCAACTCC<br>SEQ ID NO: 30 |
| Atg-5 | ATCAGACCACGACGGAGCGG<br>SEQ ID NO: 31 | GGCGACTGCGGAAGGACAGA<br>SEQ ID NO: 32 |
| Atg-12 | ACAAAGAAATGGGCTGTGGAGC<br>SEQ ID NO: 33 | GCAGTAATGCAGGACCAGTTTACC<br>SEQ ID NO: 34 |
| Gabarapl1 | CGGTCATCGTGGAGAAGGCT<br>SEQ ID NO: 35 | CCAGAACAGTATAACGGCAACTCC<br>SEQ ID NO: 36 |
| Col1a2 | GTAGCCCTGGTGAACGTGGTGAA<br>SEQ ID NO: 37 | CCATCACCACGACTTCCAACAGG<br>SEQ ID NO: 38 |
| Beta-actin | CAGGCATTGCTGACAGGATG<br>SEQ ID NO: 39 | TGCTGATCCACATCTGCTGG<br>SEQ ID NO: 40 |
| GAPDH | ATGACAATGAATACGGCTACAGCAA<br>SEQ ID NO: 41 | GCAGCGAACTTTATTGATGGTATT<br>SEQ ID NO: 42 |

Approximately 25 µl of reaction volume was used for the real-time PCR assay that consisted of 2×(12.5 µl) Brilliant SYBR Green QPCR Master mix (Applied Biosystem), 400 nM of primers (0.5 µl each from the stock), 11 µl of water, and 0.5 µl of template. The thermal conditions consisted of an initial denaturation at 95° C. for 10 min followed by 40 cycles of denaturation at 95° C. for 15s, annealing and extension at 60° C. for 1 min, and, for a final step, a melting curve of 95° C. for 15s, 60° C. for 15s, and 95° C. for 15s. All reactions were carried out in duplicate to reduce variation. Data normalization was accomplished using the endogenous control (glyceraldehyde-3-phosphate dehydrogenase or β-actin), and the normalized values were subjected to a $2^{-\Delta\Delta Ct}$ formula to calculate the -fold change between the control and experimental groups.

Western Blot. Levels of different proteins in skeletal muscle were determined by performing immunoblotting as described (Kumar et al., *FASEB J*, 17, 386-396 (2003)). Briefly, tissues were washed with phosphate-buffered saline (PBS) and homogenized in western blot lysis buffer A (50 mM Tris-Cl [pH 8.0], 200 mM NaCl, 50 mM NaF, 1 mM dithiotheritol (DTT), 1 mM sodium orthovanadate, 0.3% IGEPAL, and protease inhibitors). Approximately, 100 µg protein was resolved on each lane on 10-12% SDS-PAGE, electrotransferred onto nitrocellulose membrane, and probed using anti-Fn14 (1:1000; Cell Signaling Technology, Inc), MF-20 (1:000, Development Studies Hybridoma bank, University of Iowa), anti-laminin (1:1000; Sigma), anti-tropomyosin (1:2000, Sigma), anti-troponin (1:1000, Sigma), anti-sarcomeric α actin (1:1000, Sigma), anti nNOS (1:500, Santa Cruz Biotechnology), anti-dystrophin (1:200, Development Studies Hybridoma bank, University of Iowa), anti-MyHC-fast type (1:1000, clone BF-F3, Development Studies Hybridoma bank, University of Iowa), anti-MyHC-slow type (1:1000, clone A4.840, Development Studies Hybridoma bank, University of Iowa), anti-tubulin (1:5000, Abcam), anti-MuRF1 (1:1000, R&D Systems), anti-phospho Akt (1:500; Cell Signaling Technology, Inc), anti-phospho GSK3β (1:1000; Cell Signaling Technology, Inc), anti-phospho p70S6K (1:1000; Cell Signaling Technology, Inc), anti phospho-mTOR (1:1000; Cell Signaling Technology, Inc), anti-collagen I (1:1000; Abcam), anti-collagen III (1:1000; Abcam), and anti-collagen IV (1:500; Abcam), and detected by chemiluminescence. The bands were quantified using ImageQuant TL software (GE healthcare). To determine the levels of collagens I and III, muscle extracts were prepared in lysis buffer lacking DTT and separated on SDS-PAGE under non-reducing conditions.

Electrophoretic Mobility Shift Assay (EMSA). NF-κB activation was analyzed by EMSA as previously described (Kumar et al., *FASEB J.*, 17, 386-396 (2003)). In brief, 25 µg of nuclear extracts prepared from control or denervated muscle were incubated with 16 fmol of $^{32}$P end-labeled NF-κB or AP-1 consensus oligonucleotide (Promega) at 37° C. for 20 min, and the DNA-protein complex was resolved on a 7.5% native polyacrylamide gel. A 5% gel was used for supershift analysis. For supershift assays, nuclear extracts were first incubated with 1 µg of either anti-p50 (sc-1190×, Santa Cruz Biotechnology), anti-p52 (Cat#4882, Cell Signaling Technology), or preimmune serum (PIS) for 30 min before performing probe binding reaction. The radioactive bands from the dried gel were visualized and quantified by PhosphorImager (GE Health Care) using ImageQuant TL software.

Muscle Histology, Immunohistochemistry and Morphometric Measurements. All experiments involving the evaluation of TWEAK-Tg or TWEAK-KO and control were conducted on at least six mice per group. Hindlimb muscles (soleus, gastrocnemius, and tibial anterior) from 1 to 6 months old mice were removed, frozen in isopentane cooled in liquid nitrogen and sectioned in a microtome cryostat. For the assessment of tissue morphology or visualization of fibrosis, 10-μm-thick transverse sections of muscles were stained respectively with the Hematoxylin and Eosin (H&E) and the Sirius red (American Master Tech) and examined under a light microscope (Nikon). Amount of fibrosis in paraffin-embedded soleus muscle sections was also determined using Mason's Trichrome staining kit following a protocol suggested by manufacturer (American Master Tech).

For immunohistochemistry study, the sections were blocked in 1% bovine serum albumin in phosphate buffered saline (PBS) for 1 h, and incubated with primary antibodies in blocking solution at 4° C. overnight under humidified conditions. The sections were washed briefly with PBS before incubation with secondary antibodies for 1 h at room temperature and then washed 3 times for 30 minutes with PBS. The slides were mounted using fluorescence medium (Vector Laboratories), visualized with a fluorescent microscope (Nikon), and images were captured using Nikon DS Fi1 camera (Nikon). The primary antibodies were anti-laminin (1:100 dilution, Sigma), anti-fMHC (1:200 dilution, NCL-MHCf from Novocastra Laboratories Ltd), anti-MyHC-slow type I (1:200 dilution, Clone A4.840, Development Studies Hybridoma Bank), anti-Mac-1 (1:250 dilution, Development Studies Hybridoma Bank), anti-collagen I (1:300, Abcam), anti-collagen III (1:300, Abcam), and anti-collagen IV (1:500). Alexa Fluor® 488 or Alexa Fluor® 596-conjugated secondary antibodies (1:3000 dilution, Invitrogen) were used for detection. Fiber cross-sectional area was analyzed in H&E or laminin-stained soleus or tibial anterior muscle sections. For each muscle, the distribution of fiber cross-sectional area (CSA) was calculated by analyzing 200 to 500 myofibers using Nikon NIS Elements BR 3.00 software as described (Dogra et al., *FASEB J.*, 21, 1857-1869 (2007) and Li et al., *Hum Mol Genet.*, 18, 2584-2598 (2009)).

Skeletal Muscle Functional Analysis: The skeletal muscle force production in isometric contraction was done as previously described (Li et al., *Hum Mol Genet.*, 18, 2584-2598 (2009)). In brief, soleus muscle from control or denervated hindlimb of mice was rapidly excised and placed in Krebs-Ringer solution. The muscle was mounted between a Fort25 force transducer (World Precision Instrumentation) and a micromanipulator device in a temperature controlled myobath (World Precision Instrumentation). The muscle was positioned between platinum wire stimulating electrodes and stimulated to contract isometrically using electrical field stimulation (supramaximal voltage, 1.2-ms pulse duration) from Grass S88 stimulator. In each experiment, muscle length was adjusted to optimize twitch force (optimal length, $L_o$). The muscle was rested for 15 minutes before the tetanic protocol was started. The output of the force transducer was recorded in computer using LAB-TRAX-4 software. To evaluate a potentially different frequency response between groups, tetani were assessed by sequential stimulation at 80, 120, 150, 220, and 300 Hz with 2 minutes rest in between.

Statistical Analysis: Results are expressed as mean±S.D. The Student's t test or analysis of variance was used to compare quantitative data populations with normal distributions and equal variance. A value of $p<0.05$ was considered statistically significant unless otherwise specified.

Certain aspects of the invention are also described in Mittal et al., *J. Cell Biol*, 188, 833-849 (2010), including the Supplemental Materials, the content of which is specifically incorporated by reference.

EXAMPLE 2

Expression Fn14 is Increased in Response to Fasting/Starvation

A standard procedure was used to investigate whether expression of TWEAK or Fn14 is affected in skeletal muscle of mice in response to a mouse model of starvation. This starvation model is a model of malnutrition and anorexia, which is also common in many chronic diseases, including cancer. Accordingly, "starvation", as used herein, refers to a condition of reduced caloric intake, which reduction would typically cause loss of skeletal muscle and/or loss of force production by the skeletal muscle.

8-week old control C57BL6 mice were given access to regular water and food, or just water with no food (for starvation), for 24 hours (h) as described (see, e.g., Romanello et al., *EMBO J*, 29, 1774-1785 (2010)). The mice were then euthanized and the levels of TWEAK and Fn14 were measured by quantitative real-time PCR and Western blotting. Interestingly, fasting of mice led to a dramatic increase in mRNA levels of Fn14 in tibial anterior (TA) muscle (FIG. 21A). Furthermore, analysis of TA muscle extracts by Western blotting showed that the protein level of Fn14 was considerably increased in 24 h starved mice compared to controls (FIG. 21B). However, there was no significant change in mRNA or protein levels of TWEAK in skeletal muscle in response to starvation. These data indicate that, similar to disuse conditions, expression of Fn14 is highly up-regulated during fasting/starvation.

EXAMPLE 3

TWEAK Neutralizing Antibody Inhibits Starvation-Induced Muscle Wasting in Mice

Figure 22:
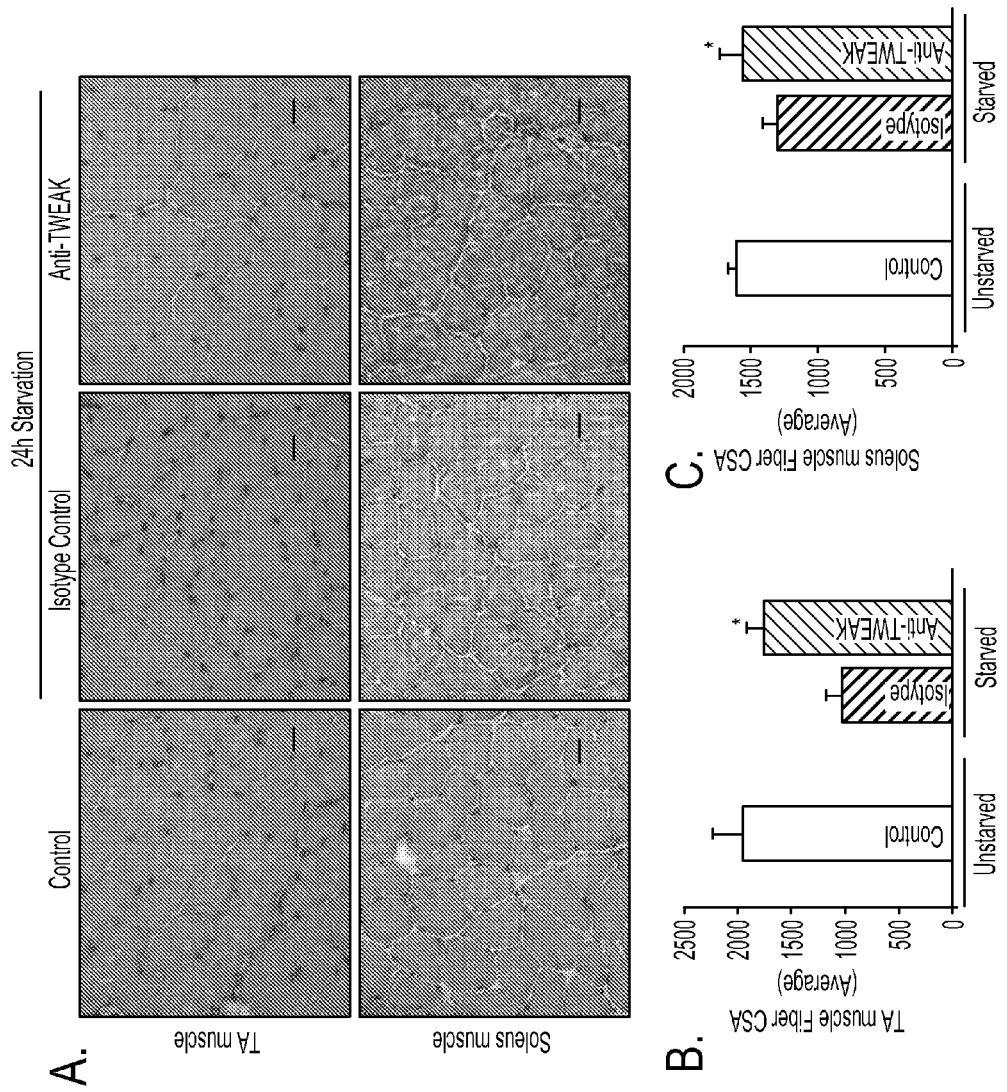
FIG. 22. Pharmacological inhibition of TWEAK inhibits starvation-induced muscle loss in mice. 8-week-old C57BL6 mice were given intraperitoneal injections of 200 μg/mouse of either rat IgG1 or an anti-TWEAK antibody every third day for 12 d (n=3 in each group) followed by starvation for 24 h. (A) Representative photomicrographs of H&E stained sections of TA and soleus muscle sections of isotype and anti-TWEAK-treated mice. Scale bar: 20 μm. Quantification of fiber CSA in (B) TA muscle, and (C) soleus muscle of mice. *p<0.05, values significantly different from isotype control-treated starved mice.

To investigate whether the TWEAK-Fn14 system is involved in skeletal muscle loss in the conditions of starvation, a commercially available TWEAK neutralization antibody (Clone MTW1; BioLegend) was used. 8-wk-old C57BL6 mice were treated by intraperitoneal injections of either 200 μg/mouse MTW1 antibody or 200 μg/ml isotype control every third day (total of three injections). After 24 h of final injection, the mice were starved for 24 h, and hind limb muscles were isolated for histological experiments. As shown in FIG. 22A, treatment with a TWEAK-neutralizing antibody improved the diameter of the fibers in both TA and soleus muscle. Furthermore, quantification of fiber cross-sectional area (CSA) in Hematoxylin and Eosin (H&E)-stained sections of TA and soleus muscle confirmed that neutralization of TWEAK activity inhibits the starvation-induced muscle atrophy in mice (FIG. 22B, C).

EXAMPLE 4

Starvation-Induced Muscle Loss is Inhibited in TWEAK-Knockout (TWEAK-KO) Mice

TWEAK-KO mice were used to investigate the role of the TWEAK-Fn14 system in skeletal muscle wasting in response to fasting. Eight-week old C57BL6 and TWEAK-KO mice were subjected to 24 h fasting, and the skeletal muscle was isolated and analyzed by biochemical and histological methods. Staining of muscle section with H&E, followed by measurement of fiber cross-sectional area, revealed that TA (FIG. 23A) and soleus muscle (FIG. 23B) fiber CSA was significantly preserved in TWEAK-KO mice compared to control mice 24 h after fasting.

Figure 23:
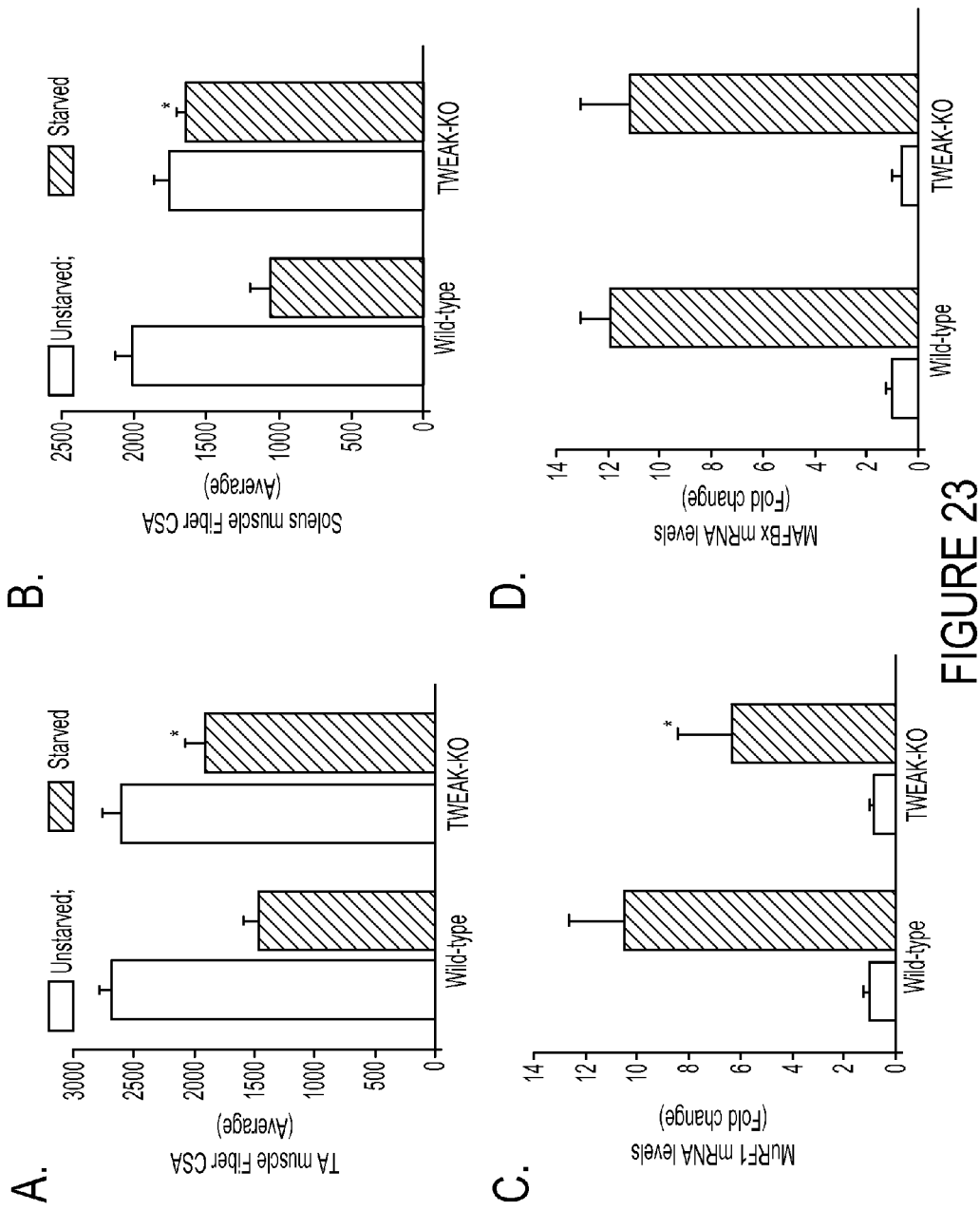
FIG. 23. Genetic deletion of TWEAK inhibits starvation-induced muscle atrophy. 8-week-old wild-type and TWEAK-KO mice were starved for 24 h and the skeletal muscle tissues isolated were analyzed by histomorphometric and biochemical methods. Quantification of fiber CSA of H&E-stained sections of (A) TA, and (B) Soleus muscle of 24 h starved wild-type and TWEAK-KO mice. The mRNA levels of (C) MuRF1, and (D) MAFBx in TA muscle of unstarved and starved wild-type and TWEAKKO mice. Error bars represent the SD. *p<0.05, values significantly different from starved wild-type mice.

Published reports suggest that in almost all muscle-wasting conditions, the expression of two muscle E3 ubiquitin ligases (MuRF1 and MABx) is significantly elevated and these ligases mediate the muscle proteolysis (4-6). Whether TWEAK-Fn14 dyad regulates the expression of these two ligases in the conditions of starvation was investigated. Interestingly, the starvation-induced expression of MuRF1 was found to be significantly inhibited in TWEAK-KO mice compared to wildtype mice (FIG. 23C). On the other hand, there was no significant difference in the transcript levels of MAFBx in skeletal muscle of TWEAK-KO and wild-type mice fasted for 24 h (FIG. 23D). These data indicate that TWEAK could be inducing muscle loss through up-regulation of MuRF1 in the conditions of starvation.

EXAMPLE 5

Expression of Fn14 is Upregulated in Skeletal Muscle of Diabetic Mice

Figure 24:
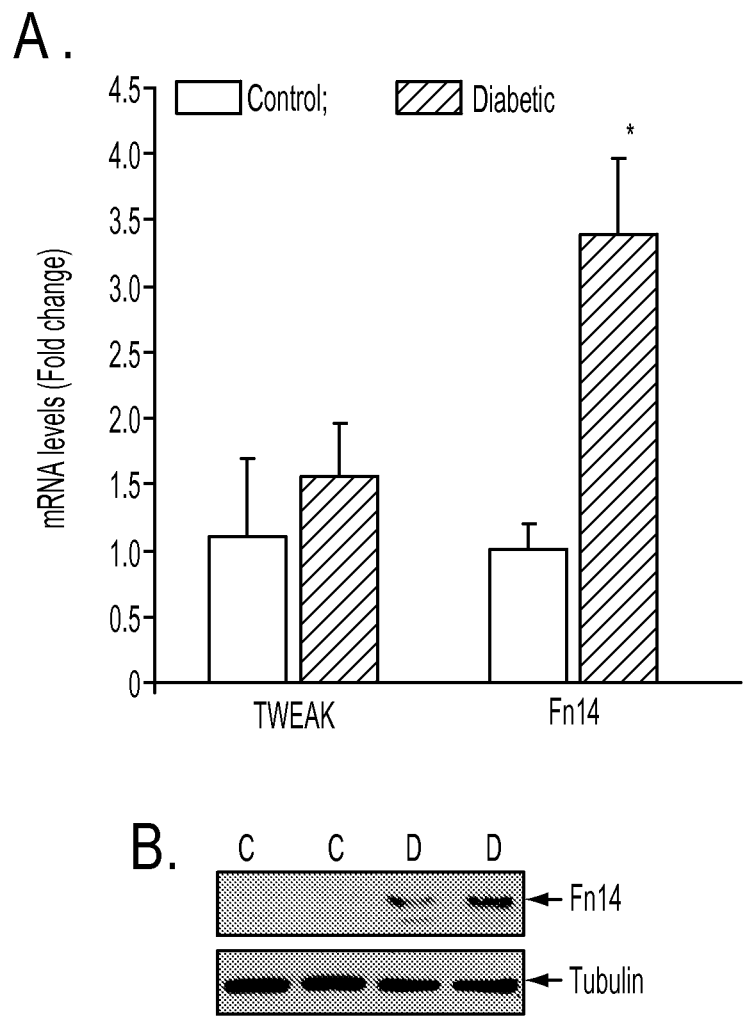
FIG. 24. Increased expression of Fn14 in skeletal muscle of diabetic mice. 6-weeks old C57BL6 mice were subjected to the conditions of diabetes, and TA muscle isolated was used to study the expression of TWEAK and Fn14. (A) Fold change in mRNA levels of TWEAK and Fn14 in TA muscle of control and diabetic mice. Bars represent SD. *p<0.05, values significantly different from control (vehicle alone treated) mice. (B) Western blot analyses of protein levels of Fn14 in TA muscle of control and diabetic mice. C, control; D, diabetic.

Whether the expression of TWEAK or Fn14 is affected in skeletal muscle of diabetic mice was investigated. Type I diabetes was induced in 6-wk-old male C57BL6 mice by repeated low-dose Streptozotocin (STZ, 55 mg/kg/d for six consecutive days, i.p.) treatment as described previously (Baba et al., *Diabetes*, 58, 2486-2497 (2009)). Mice treated with vehicle only (0.05 mM sodium citrate, pH 4.5) served as controls. 1 wk after the last injection of STZ, blood was collected from the tail vein. All the STZ-injected mice had blood glucose>400 mg/dL. Mice were sacrificed 5 d after measuring the blood glucose levels and skeletal muscle isolated was analyzed for the expression of TWEAK and Fn14. The mRNA levels of Fn14, but not TWEAK, were significantly elevated in diabetic mice compared to control mice (FIG. 24A). Furthermore, the protein levels of Fn14 were also found to be elevated in skeletal muscle of diabetic mice (FIG. 24B). These data indicate that, similar to disuse and starvation conditions, the TWEAK-Fn14 system appears to be a mediator of muscle loss in diabetic patients.

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for reducing loss of skeletal muscle in a patient having a battlefield injury, an accidental injury, cancer, anorexia or diabetes, comprising administering to a patient having a battlefield injury, an accidental injury, cancer, anorexia or diabetes a therapeutically effective amount of an agent that decreases the activity of the TWEAK/Fn14 system so as to reduce the loss of skeletal muscle, wherein the agent is a TWEAK neutralizing antibody that blocks TWEAK activity.

2. The method of claim 1, wherein the patient has a battlefield or accidental injury.

3. The method of claim 2, wherein the patient has a battlefield injury.

4. The method of claim 1, wherein the patient has cancer.

5. The method of claim 1, wherein the patient has anorexia.

6. The method of claim 1, wherein the patient has diabetes.

7. The method of claim 6, wherein the patient has type II diabetes.

8. The method of claim 1, wherein the skeletal muscle is a soleus, tibial anteriors, gastrocnemius, EDL, diaphragm, biceps, triceps, quadriceps, facial, tongue, or abdominal muscle.

9. The method of claim 1, wherein the administration of the therapeutically effective amount of an agent that decreases the activity of the TWEAK/Fn14 system also reduces the loss of force production by the skeletal muscle.

10. A method for reducing loss of force production by skeletal muscle in a patient having a battlefield injury, an accidental injury, cancer, anorexia or diabetes, comprising administering to a patient having a battlefield injury, an accidental injury, cancer, anorexia or diabetes a therapeutically effective amount of an agent that decreases the activity of the TWEAK/Fn14 system so as to reduce the loss of force production by the skeletal muscle, wherein the agent is a TWEAK neutralizing antibody that blocks TWEAK activity.

11. The method of claim 10, wherein the patient has a battlefield or accidental injury.

12. The method of claim 11, wherein the patient has a battlefield injury.

13. The method of claim 10, wherein the patient has cancer.

14. The method of claim 10, wherein the patient has anorexia.

15. The method of claim 10, wherein the patient has diabetes.

16. The method of claim 15, wherein the patient has type II diabetes.

17. The method of claim 10, wherein the skeletal muscle is a soleus, tibial anteriors, gastrocnemius, EDL, diaphragm, biceps, triceps, quadriceps, facial, tongue, or abdominal muscle.

* * * * *

SEQUENCE LISTING

```
<160> NUMBER OF SEQ ID NOS: 42

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gctacgaccg ccagattggg                                                   20

<210> SEQ ID NO 2
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 2
gccagcacac cgttcaccag                                                      20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aagtgcatgg actgcgcttc tt                                                   22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggaaactaga aaccagcgcc aa                                                   22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cggcaatgag tacgtcacca aa                                                   22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcaaagccag cgatgtccaa                                                      20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaccgaatac aggctgacga tg                                                   22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 8
gggcacggat tcattccttt                                                      20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtcgcagcca agaagagaaa ga                                                   22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgctatcagc tccaacagcc tt                                                   22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
taactgcatc tccatgctgg tg                                                   22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tggcgtagag ggtgtcaaac tt                                                   22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcatgatccg cgacgtggaa                                                      20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 14
agatccatgc cgttggccag                                              20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agggttgtcc agccgatgat at                                           22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cccagcttct tgacgttgtt ga                                           22

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttactctcct gccatccttc acga                                         24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccatttgtgg tgggagaaac tgtg                                         24

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctccatgagc tttgtacaag g                                            21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 20
tgctgatgta ccagttgggg					20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccttcttggg actgatgctg g					21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcctccgact tgtgaagtgg t					21

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aaccagttcc aacgctacct ga				22

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agaaagaacc ctgcatggca					20

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
taagtgccat cccaaggaca ctct				24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cccagtgatg tcactccaac aatc						24

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctggtgaatg ggcacagcat g						21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgtccgctgg taacatccct t						21

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgaaatcaat gctgcctggg						20

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccagaacagt ataacggcaa ctcc						24

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atcagaccac gacggagcgg						20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggcgactgcg gaaggacaga                                              20

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
acaaagaaat gggctgtgga gc                                           22

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gcagtaatgc aggaccagtt tacc                                         24

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cggtcatcgt ggagaaggct                                              20

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccagaacagt ataacggcaa ctcc                                         24

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gtagccctgg tgaacgtggt gaa                                          23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccatcaccac gacttccaac agg                                          23

-continued

```
<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
caggcattgc tgacaggatg                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tgctgatcca catctgctgg                                              20

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
atgacaatga atacggctac agcaa                                        25

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gcagcgaact ttattgatgg tatt                                         24
```